(12) United States Patent
Gajic et al.

(10) Patent No.: US 10,460,408 B2
(45) Date of Patent: Oct. 29, 2019

(54) PRESENTATION OF CRITICAL PATIENT DATA

(75) Inventors: Ognjen Gajic, Rochester, MN (US); Vitaly Herasevich, Marshfield, WI (US); Brian W. Pickering, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 238 days.

(21) Appl. No.: 12/697,861

(22) Filed: Feb. 1, 2010

(65) Prior Publication Data
US 2010/0198622 A1    Aug. 5, 2010

Related U.S. Application Data

(60) Provisional application No. 61/148,953, filed on Jan. 31, 2009.

(51) Int. Cl.
    *G06Q 50/00*    (2012.01)
    *G06Q 50/22*    (2018.01)
    *G06Q 50/24*    (2012.01)

(52) U.S. Cl.
    CPC ............ *G06Q 50/22* (2013.01); *G06Q 50/24* (2013.01)

(58) Field of Classification Search
    USPC .......................................... 705/2–4; 715/744
    See application file for complete search history.

(56) References Cited

U.S. PATENT DOCUMENTS

| 5,140,519 | A | 8/1992 | Friesdorf et al. |
| 5,912,656 | A | 6/1999 | Tham et al. |
| 5,921,920 | A | 7/1999 | Marshall et al. |
| 6,322,502 | B1 | 11/2001 | Schoenberg et al. |
| 6,804,656 | B1 | 10/2004 | Rosenfeld et al. |
| 7,374,535 | B2 | 5/2008 | Schoenberg et al. |
| 7,433,827 | B2 | 10/2008 | Rosenfeld et al. |
| 7,627,334 | B2 * | 12/2009 | Cohen et al. ............ 455/456.3 |
| 7,778,851 | B2 * | 8/2010 | Schoenberg et al. ............ 705/3 |
| 7,899,683 | B2 * | 3/2011 | Schoenberg et al. ............ 705/2 |

(Continued)

FOREIGN PATENT DOCUMENTS

WO    WO 02/056151    7/2002

OTHER PUBLICATIONS

Ball, Marion J., N. C. M. N. Carla Smith, and Richard S. Bakalar. "Personal health records: empowering consumers." Journal of Healthcare Information Management 21.1 (2007): 77.*

(Continued)

*Primary Examiner* — Mark Holcomb
(74) *Attorney, Agent, or Firm* — Headland Law & Strategy

(57) ABSTRACT

A computer-implemented patient information presentation method is disclosed. The method includes extracting, from records maintained for a patient under care in a healthcare facility, a subset of data points for that patient that are determined to represent data points of highest relevance to a subset of potential caregivers for the patient. The method also includes grouping the subset of data points into a plurality of groups based on a determined relatedness among data points in each of the plurality of groups, and generating a display for presentation to a caregiver that shows at least some of the subset of data points arranged in the groups.

24 Claims, 21 Drawing Sheets

(56) References Cited

U.S. PATENT DOCUMENTS

| | | | |
|---|---|---|---|
| 2003/0225597 A1* | 12/2003 | Levine | G06Q 10/10 705/3 |
| 2005/0125256 A1 | 6/2005 | Schoenberg et al. | |
| 2006/0143093 A1* | 6/2006 | Brandt et al. | 705/26 |
| 2006/0161459 A9 | 7/2006 | Rosenfeld et al. | |
| 2006/0229917 A1 | 10/2006 | Simske et al. | |
| 2007/0129970 A1* | 6/2007 | Haider | 705/3 |
| 2007/0249951 A1 | 10/2007 | Nieman et al. | |
| 2008/0072901 A1 | 3/2008 | Habashi | |
| 2008/0208618 A1 | 8/2008 | Schoenberg et al. | |
| 2008/0281219 A1 | 11/2008 | Glickman et al. | |
| 2009/0216556 A1* | 8/2009 | Martin | G06Q 50/24 705/3 |
| 2009/0217194 A1* | 8/2009 | Martin et al. | 715/783 |
| 2010/0179835 A1* | 7/2010 | Wager | G06Q 10/10 705/3 |
| 2010/0312798 A1* | 12/2010 | Dutta | G16H 50/70 707/780 |

OTHER PUBLICATIONS

'Access Medicine' [online]. "Principles of Critical Care: Chapter 37 Ventilator-Induced Lung Injury," Retrieved on Feb. 3, 2010, Retrieved from the Internet <URL:http://www.accessmedicin.com/pop.aspx?aID=2287452&print=yes>. 27 pages.

Afessa, "Evaluating the performance of an Institution Using an Intensive Care Unit Benchmark," *Mayo Clin Proc.*, 2005, 80(2):174-180.

Arora et al., "Communication failures in patient sign-out and suggestions for improvement: a critical incident analysis," *Qual Saf Health Care*, 2005, 14(6):401-407.

Bhabra et al., "An experimental comparison of handover methods," *Ann R Coll Surg Engl.*, 2007, 89(3):298-300.

U.S. Appl. No. 60/141,520, Rosenfeld, filed Jun. 23, 1999.

Bomba and Prakash, "A description of handover processes in an Australian public hospital," *Aust Health Rev.*, 2005, 29(1):68-79.

Byrnes et al., "Implementation of Mandatory Checklist of Protocols and Objectives Improves Compliance With a Wide Range of Evidence-Based Intensive Care Unit Practices," *Crit. Care Med.*, 2009, 37(10):2775-2781.

Catchpole et al., "Patient handover from surgery to intensive care: using Formula 1 pit-stop and aviation models to improve safety and quality," *Paediatr Anaesth.*, 2007, 17(5):470-478.

Chedoe et al., "Incidence and nature of medication errors in neonatal intensive care with strategies to improve safety: a review of the current literature," *Drug Saf.*, 2007, 30(6):503-513.

Dubose et al., "Measurable Outcomes of Quality Improvement in the Trauma Intensive Care Unit: The Impact of a Daily Quality Rounding Checklist," *The Journal of TRAUMA: Injury, Infection, and Critical Care*, Jan. 2008, 64(1):22-29.

Egan, "Clinical Dashboards: Impact on Workflow, Care Quality, and Patient Safety," *Crit Care Nurs Q*, 2006, 29(4):354-361.

Harrison et al., "Time to hand over our old way of working?" *Hosp Med.*, 2005, 66(7):399-400.

Montgomery, "Effect of fatigue, workload, and environment on patient safety in the pediatric intensive care unit," *Pediatr Crit Care Med.*, 2007, 8(2 Suppl):S11-S16.

Pickering et al., "Identifying Differences in Patient Data Utilization Between Physician Grades at the Time of Admission to the ICU," International Anesthesia Research Society Abstract 09-A-1810-IARS, Nov. 15, 2008, 3 pages.

Pickering et al., "Patient Data Utilization at Intensive Care Unit Admission," ATS 2009, San Diego International Conference, 2009, Abstract Number: 956580, 2 pages.

Pronovost et al., "Interventions to Reduce Mortality Among Patients Treated in Intensive Care Units." *Journal of Critical Care*, Sep. 2004, 19(3):158-164.

Roughton and Severs, "The junior doctor handover: current practices and future expectations," *J R Coll Physicians Lond.* 1996, 30(3):213-214.

Stahl et al., "Enhancing Patient Safety in the Trauma/Surgical Intensive Care Unit." *The Journal of TRAUMA: Injury, Infection, and Critical Care*, Sep. 2009, 67(3):430-435.

Wahl et al., "Use of Computerized ICU Documentation to Capture ICU Core Measures," *Surgery*, 2006. 120(4):684-690.

International Search Report and Written Opinion in International Application No. PCT/US2010/022750, dated Aug. 25, 2010, 10 pages.

International Preliminary Report on Patentability in International Application No. PCT/US2010/022750, dated Aug. 11, 2011, 6 pages.

* cited by examiner

PATIENT 1

Stent

| | | | |
|---|---|---|---|
| Fluid Bolus | 4L | Hb | 10 |
| NE | 0.02 | Blood Loss | 100 |
| Dopamine | 0.08 | Hct | 0.27 |
| NE | 0 | X Match | Yes |
| aVP | 0 | IV Access | 16G x2 |

Obese
COPD
Smoker

| | | CXR | Infiltrate |
|---|---|---|---|
| RR | 28 | pH | 7.28 |
| SpO2 | 92 | pCO2 | 55 |
| PaO2/FiO2 | 148 | HCO3 | 36 |
| O2 | 10L | pO2 | 89 |
| NIVV | No | Value | |
| IVV | No | Value | |

| | T°C | 38.9 | Cultures Tak. | Yes |
|---|---|---|---|---|
| | WBC | 15 | Source Cont. | No |
| Antimicrobial | Date | | Source | Organism |
| Vancomycin | 1 N/A | | N/A | N/A |
| Zosyn | 2 N/A | | N/A | N/A |
| None | 3 N/A | | N/A | N/A |

Alcoholism

| | | | |
|---|---|---|---|
| UOP ml/hr | 25 | K+ | 4 |
| Creatinine | 1.8 | Lactate | N/A |
| Fluid Balance | 3000 | Base Deficit | N/A |
| | | Glucose | N/A |

GCS 15

DM

Possible Cardiac
ST Change
Troponin Rise

Possible Hemorrhage
Blood Loss

SOFA: CVS, RESP, RENAL, CNS, LIVER, COAG

FIG. 3A-2

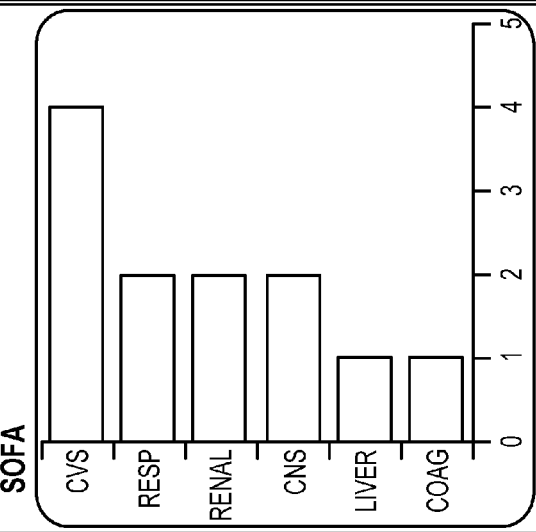

PATIENT 2

| Stent | | | | |
|---|---|---|---|---|
| | Fluid Bolus | 4L | Hb | 10 |
| | NE | 0 | Blood Loss | 0 |
| | Dopamine | 0 | Hct | 0.27 |
| | NE | 0 | X Match | Yes |
| | aVP | 0 | IV Access | 20G x2 |

Obese / COPD / Smoker

| RR | 16 | | CXR | Infiltrate |
|---|---|---|---|---|
| SpO2 | 100 | | pH | 7.4 |
| PaO2/FiO2 | 762 | | pCO2 | 45 |
| O2 | 10L | | HCO3 | 34 |
| NIVV | No | Value | pO2 | 160 |
| IVV | No | Value | | |

Alcoholism

| T°C | 38.9 | | Cultures | Yes |
|---|---|---|---|---|
| WBC | 10 | | Source C | No |
| Antimicrobial | Date | | Source | Organism |
| 1 None | 1 N/A | | N/A | N/A |
| 2 None | 2 N/A | | N/A | N/A |
| 3 None | 3 N/A | | N/A | N/A |

DM

| UOP ml/hr | 40 | K+ | 4 |
|---|---|---|---|
| Creatinine | 1.4 | Lactate | N/A |
| Fluid Balance | 3000 | Base Def | N/A |
| | | Glucose | N/A |

| GCS | 14 |
|---|---|

PATIENT 3

◯ Known CCF
♥ Known IHD
Hypertension ST△
Stent

| HR A Fib 110 | EKG Done | STChange |
|---|---|---|
| MAP 60 | ECHO N/A | 0 |
| ST△ Yes | Troponin Done | 0.8 |

| Fluid Bolus 6L | Hb | 7 |
| NE 0.5 | Blood Loss | 0 |
| Dopamine 15 | Hct | 0.27 |
| NE 0 | X Match | Yes |
| aVP 0.03 | IV Access 20G | x2 |

SHOCK

Possible Sepsis
HR>90
T>38.4

Possible Cardiac
ST Change
Troponin Rise

🫁 Obese
COPD
Smoker

| RR | 16 | | CXR | Effusion |
|---|---|---|---|---|
| SpO2 | 90 | | pH | 7.1 |
| PaO2/FiO2 | 200 | | pCO2 | 45 |
| O2 | 0.5 | | HCO3 | 34 |
| NIVV | Yes | | pO2 | 100 |
| IVV | No | Value Value | | |

🍷 Alcoholism

| T°C | 38.9 | Cultures Tak. | Yes |
|---|---|---|---|
| WBC | 3 | Source Cont. | No |

Antimicrobial Date Source Organism
| None | 1 N/A | N/A | N/A |
| None | 2 N/A | N/A | N/A |
| None | 3 N/A | N/A | N/A |

🧠 DM

| UOP ml/hr | 10 | K+ | 5.5 |
|---|---|---|---|
| Creatinine | 2.4 | Lactate | N/A |
| Fluid Balance | 7000 | Base Deficit | N/A |
| | | Glucose | N/A |

GCS 12

SOFA

(bar chart with bars for CVS≈4.5, RESP≈2, RENAL≈2, CNS≈2, LIVER≈1, COAG≈1; y-axis 0–5)

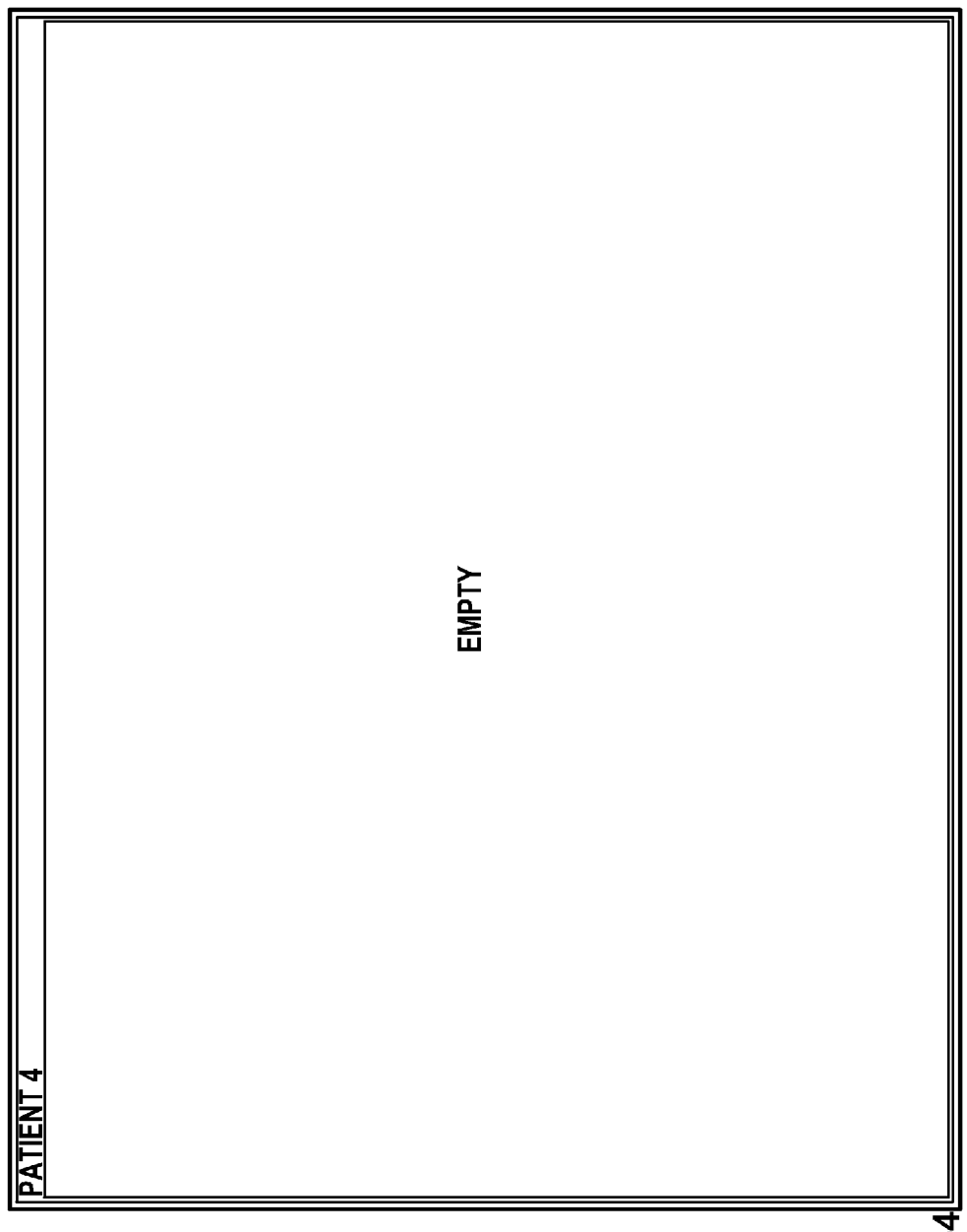

FIG. 3C

| SHOCK | | | | | |
|---|---|---|---|---|---|
| Primary | Trigger | Rule | | Display Value | Syndrome Advisory |
| Sepsis | MAP<65mmHg | 1 | | SHOCK | |
| | HR >90 | 1 | 0 | HR >90 | ?Sepsis |
| | T >38.4 | 0 | 1 | WBC >12 | Possible Sepsis |
| | WBC >12 | 1 | 0 | | |
| | WBC <4 | 0 | | | |
| | T NA | 1 | | | |
| | WBC NA | 1 | | | |
| Hemorrhage | Blood Loss | 1 | | Blood Loss | ?Hemorrage |
| | | | | | Possible Hemorrage |
| Cardiac | ST Change | 1 | | ST Change | ?Cardiac |
| | Troponin Rise | 0.06 | | Troponin Rise | Possible Cardiac |

FIG. 3H

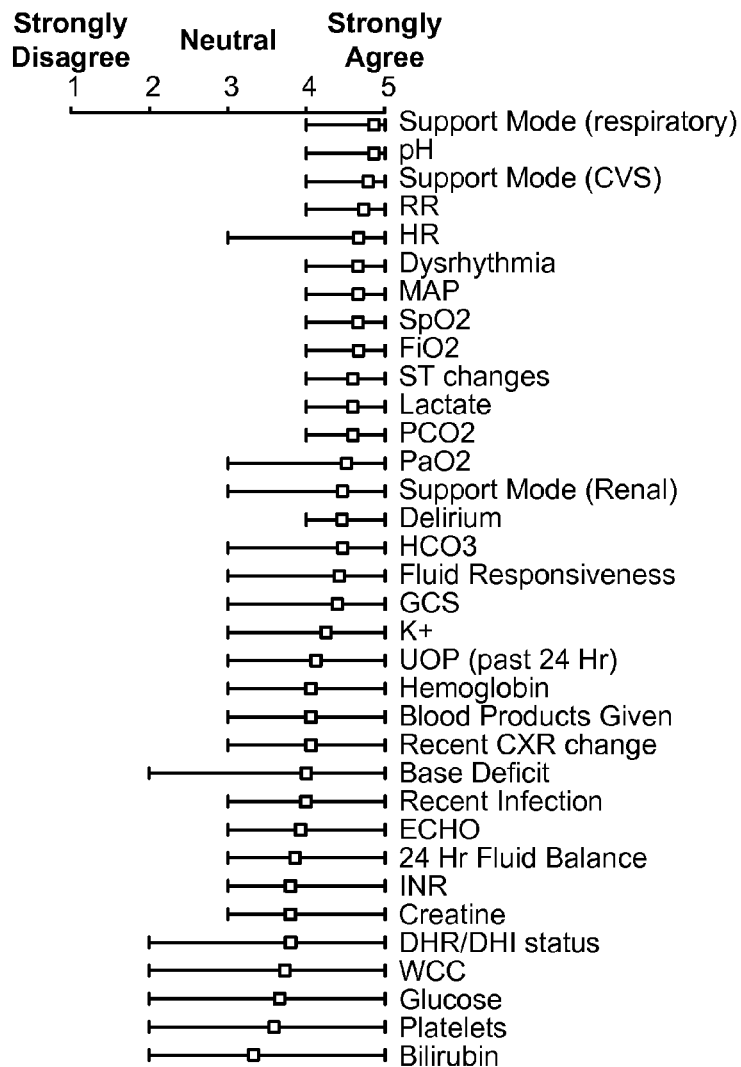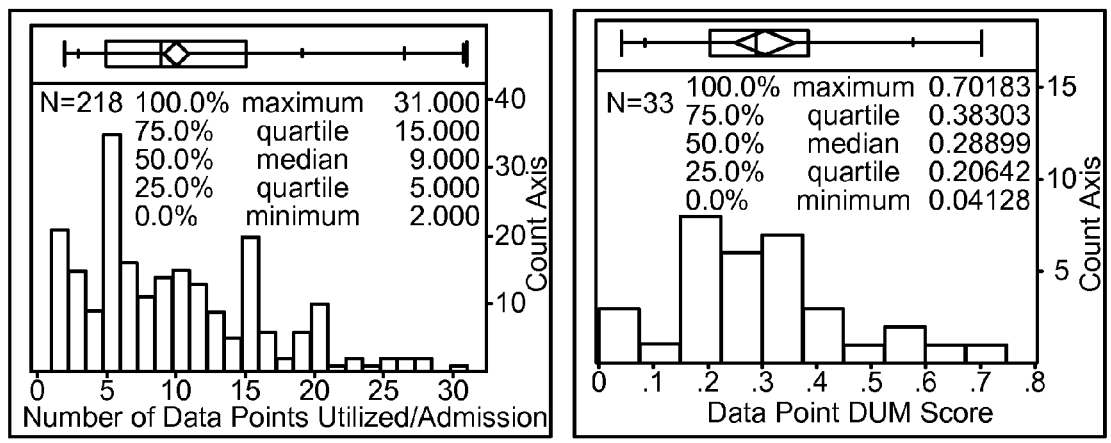
FIG. 5

10.02.2009 AWARE has detected the following on Mr Jones 701
702 — Ventilated
703 — HOB is at 30 degrees
704 — Lansoprazole 30mg bid given at 9:00
     — Heparin 5,000 iu BID sc given at 9:30
705 — Sedation Break Appropriate?
        — Propofol 5mcg/kg/min
          RASS-2
706 — CAM ICU negative
        — Sedation last held at 6:00am for 2 hours
707 — Ventilator Order Current?
        Mode    IMV
        Rate    20
708 — TV      6 ml/kg (350ml)
        PEEP    10 cm

Respiratory Weaning Assessment?

709
710 — IV Devices Needed? 711   712   713
     Name      Site     Inserted    Site
     1. PICC   RACF     10.01.2009  WNL
     2. CVL    RIJ      09.20.2009  Red
     3. Art    R Rad    09.20.2009  WNL WBC 16    Temperature 38.0    Microbiology 3 — 721

| Description | Rule | Secondary Rule | Displayed | Time Rg. |
|---|---|---|---|---|
| Ventilated | If Ventilator Mode is " " or "BIPAP" then indicator is RED, ELSE GREEN | If indicator Green then Display ventilator Checklist | Most recent | 2 hour |
| HOB | If HOB equals 30 degrees or greater at any point in past 24 hours then indicator is GREEN else RED | Determine the percentage of time the HOB is detected as > 30 degrees in previous 24 hours - For reporting | Most recent | 4 hours |
| Ulcer Prophylaxis | Search MAR for Omeprazole Ranitidine Lansoprazole Famotidine Pantoprazole Cimetidine Esomeprazole Nizatidine Rabeprazole | Display Detected AGENT, DOSE, administration schedule and administration time OR None if none detected | Last Administered | 24 hours |
| DVT Prophylaxis | Search MAR for Heparin OR Argatroban SC/SQ or IVI OR enoxaparin and SC/SQ OR dalteparin and SC/SQ AND part string 'SCD' from Viewers/ reports/cardiovascular/ Vascular Aids -Types | Display Detected AGENT, DOSE, administration schedule and administration time AND SCD plus location (Viewers/reports/ cardiovascular/Vascular Aids ON/OFF) Or none if none detected | Last Administered | 24 hours |
| Sedation | Search IVI for agents listed in CNS supports rules (4 hours)=Active agents AND search for agents running in past 24 hours= All agents | If ACTIVE agent detected display agent type and dose mcg/kg/min ELSE display "No IV sedation detected in past 4 hours" AND IF "All Agent" detected display "AGENT X discontinued at T= time discontinued" | Active, Discontinued in past 24 hours | 4 hours |
| Sedation Break | If ACTIVE agent is detected to be running for >24 hours, determine if there were any breaks > 1 hour in the past 24 hours. IF Active Agent is running < 24 hours display "AGENT X" running less than 24 hours, ELSE IF agent running > 24 hours and no breaks detected display "No Break in AGENT X Detected in past 24 hours". | IF Break is detected THEN display AGENT X last held at "T- break time start" for "Break time finish - break time start" hours | See secondary rule | 24 hours |
| Ventilator Order Current? | Pull ventilator setting as stipulated in support rules | Display Mode, Set Rate, TV and PEEP | Most recent | 4 hours |
| TV | TV = TV/PBW ml/kg (TV ml). IF Gender = "M" then PBW = 50+0.91*(height (cm)- 152.4) ELSE IF gender = "F" then PBW = 45.5+0.91*(height (cm)-152.4) | | Most recent | 4 hours |

FIG. 8A

| | | | | |
|---|---|---|---|---|
| IV Devices Needed | Display IV checklist if central IVI devices detected | | Always if any CVL detected | 4 hours |
| Name | Viewers Labs \Hospital Chart\IV incisions Drains\IV device\Name | | If available | 4 hours |
| Site | Viewers Labs\Hospital Chart\IV incisions Drains\IV device\site | | If available | 4 hours |
| Inserted | Viewers Labs\Hospital Chart\IV incisions Drains\ IV device\ insert date | | If available | 4 hours |
| Site Condition | Viewers Labs\Hospital Chart\IV incisions Drains\IV device\ skin condition | | If available | 4 hours |
| HOB indicator | If HOB equals 30 degrees or greater at any point in past 24 hours then indicator is GREEN else RED | | | 24 hours |
| Ulcer prophylaxis indicator | If any agents listed in 3 are detected as administered in past 12 hours then indicator is GREEN else RED | | | 24 hours |
| DVT prophylaxis indicator | If any MAR agents listed in 3 are detected as administered in past 12 hours then indicator is GREEN else RED | | | 24 hours |
| Sedation Break indicator | Manual input | | | |
| Ventilation order indicator | Manual input | | | |
| Weaning indicator | Manual input | | | |
| IV devices indicator | IF current date - insert date >6 days OR IF site condition DOES NOT Equal "WNL" then indicator is RED else GREEN | | If available | 24 hours |
| Infection information | Same rules as defined in INFX physiology rules | Vital Signs | Most recent | 24 hours |

FIG. 8B

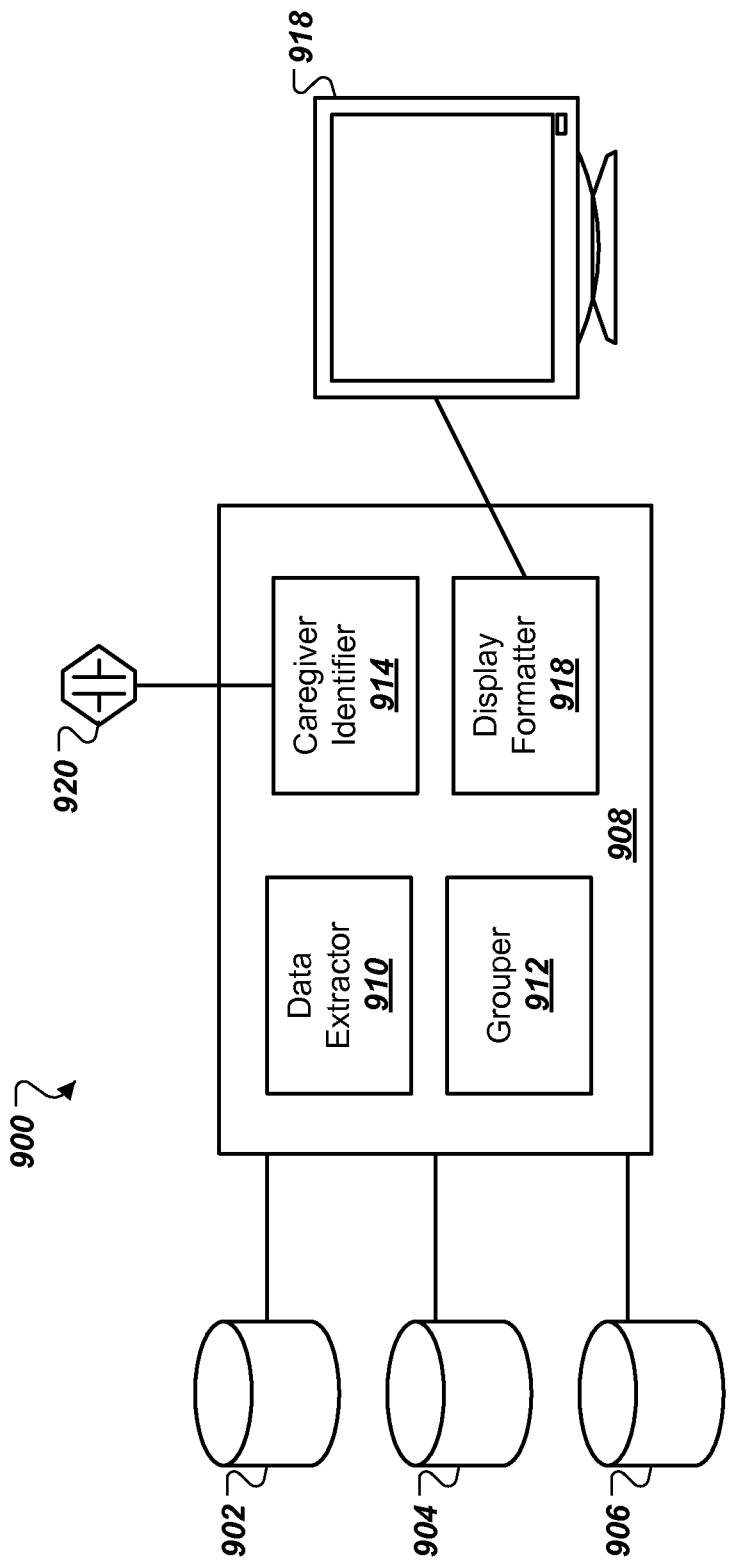

PRESENTATION OF CRITICAL PATIENT DATA

CROSS-REFERENCE TO RELATED APPLICATIONS

This application claims priority to U.S. Provisional Patent Application Ser. No. 61/148,953 to Ognjen Gajic et al., entitled "Presentation of Critical Patient Data," and filed Jan. 31, 2009, the contents of each are incorporated herein by reference.

TECHNICAL FIELD

This document relates to computer-based systems and techniques for providing information about the clinical status of a patient, such as a patient in an intensive care unit (ICU), and of making clinical decisions for treating the patient.

BACKGROUND

The care of critically ill patients generates vast quantities of clinical data. These data are processed by an ICU team and are the basis of subsequent medical decision making. Data overload is a phenomenon whereby the significance of data (signal) is lost within an overwhelming quantity of insignificant data (noise). The quantities of data generated in the ICU can, at times, overwhelm a physician's personal capacity to identify and then process relevant data. This may lead to errors of clinical judgment or delays in the delivery of time sensitive interventions.

SUMMARY

This document describes systems and techniques that may be used to provide information about patient status, such as an ICU patient, to members of a medical team. ICU's are busy places that generate a lot of patient data, and caregivers such as physicians may easily become overwhelmed with information. The systems and techniques described here aim to identify the most important data, to group it in manners that are intuitive for a caregiver, and to display or otherwise present the information in an efficient and effective manner to the caregiver. The process of identifying the most important data may occur by filtering all of the data being gathered on a patient to isolate data relating to features of the patient that expert physicians most often review for patients in a situation like the particular monitored patient. Data of a particular type may then be gathered together into groups, such as data relating to a particular body organ or function. The data groups may then be presented graphically and textually in a manner that improves the ability of a caregiver to quickly understand the current and past state of a patient and to make clinical decisions that will benefit the patient.

In certain implementations, such systems and technique may provide one or more advantages. For example, patient care and safety may be improved when a caregiver can make better medical judgments from well-selected and well-formatted information. Also, caregivers may be able to provide additional care if they are able to discern a patient's overall status more quickly because they have been presented relevant data in an understandable manner. Moreover, caregiver fatigue may be lessened and caregiver satisfaction improved when useful and pleasing systems are provided to caregivers, and caregivers are not forced to struggle to complete tasks that should be conducted for them, such as identifying the most relevant data for a patient.

In one implementation, a computer-implemented information presentation method is disclosed. The method comprises extracting, from records maintained for a patient under care in a healthcare facility, a subset of data points for that patient that are determined to represent data points of highest relevance to a subset of potential caregivers for the patient. The method also comprises grouping the subset of data points into a plurality of groups based on a determined relatedness among data points in each of the plurality of groups, and generating a display for presentation to a caregiver that shows at least some of the subset of data points arranged in the groups. The method can also include identifying a plurality of subset groups of the data points, where each of the plurality of subset groups is directed to a particular caregiver level that differs from others of the plurality of subset groups. The subset groups can be directed to different job titles of caregivers.

In some aspects, the method also includes detecting the presence of an electronic caregiver beacon in proximity to a patient monitor, determining a caregiver level corresponding to a caregiver associated with the beacon, and displaying a subset of data points directed to the determined caregiver level corresponding to the caregiver. The caregiver beacon can comprise an identification badge or biometric indicator. In another aspect, the records are stored in a plurality of separate and independent data stores, including a real time patient condition data store and an electronic medical record data store. Also, the subset of data points can be selected as data points having a highest frequency of reliance by experienced caregivers in a group of caregivers having a common job categorization.

The method can also comprise detecting one or more indicia of organ failure and changing a display mode presented to the caregiver to provide information targeted to the organ failure and to deprecate other information previously displayed on a display. In addition, the method can comprise performing an identification of a caregiver in proximity to a patient monitor and generating the display for presentation to the caregiver according to a custom layout for the caregiver. The method can also comprise detecting the task that the user is undertaking and reconfiguring the display to optimize the performance of that task (task specific modules—sepsis and checklist are given for illustrative purposes)

In another implementation, a computing system is disclosed that comprises a patient video monitor, one or more processors, memory, and one or more programs. The one or more programs are stored in the memory and are configured to be executed by the one or more processors. The programs include instructions for extracting, from records maintained for a patient under care in a healthcare facility, a subset of data points for that patient that are determined to represent data points of highest relevance to a subset of potential caregivers for the patient. The programs also include instructions for grouping the subset of data points into a plurality of groups based on a determined relatedness among data points in each of the plurality of groups, and instructions for generating a display for presentation to a caregiver that shows at least some of the subset of data points arranged in the groups.

In yet another implementation, a computer-implemented patient information presentation system is disclosed. The system comprises a data extractor operating on a computer processor system programmed to analyze a plurality of independent data sources to obtain a subset of data about a patient, from the data sources, using heuristic rules directed to patient data points of highest relevance to a subset of potential caregivers for the patient. The system also comprises a data grouper operating on the computer processor system, and an electronic patient monitor to receive display data from the computer processor system and to display group patient information for at least some of the subset of data The details of one or more embodiments are set forth in the accompanying drawings and the description below. Other features and advantages will be apparent from the description and drawings, and from the claims.

DESCRIPTION OF DRAWINGS

FIGS. 3A to 3H show example displays that may be shown to caregivers in an ICU setting.

FIG. 5 shows data representing a survey of physician preferences for data points in an ICU setting.

FIG. 7 shows an example screen shot, or display, of a patient monitoring interactive checklist.

FIGS. 8A and 8B are two portions of a table of example values for the patient monitoring interactive checklist of FIG. 7

FIG. 9 is a block diagram of a patient monitoring system.

Like reference symbols in the various drawings indicate like elements.

DETAILED DESCRIPTION

Figure 1:
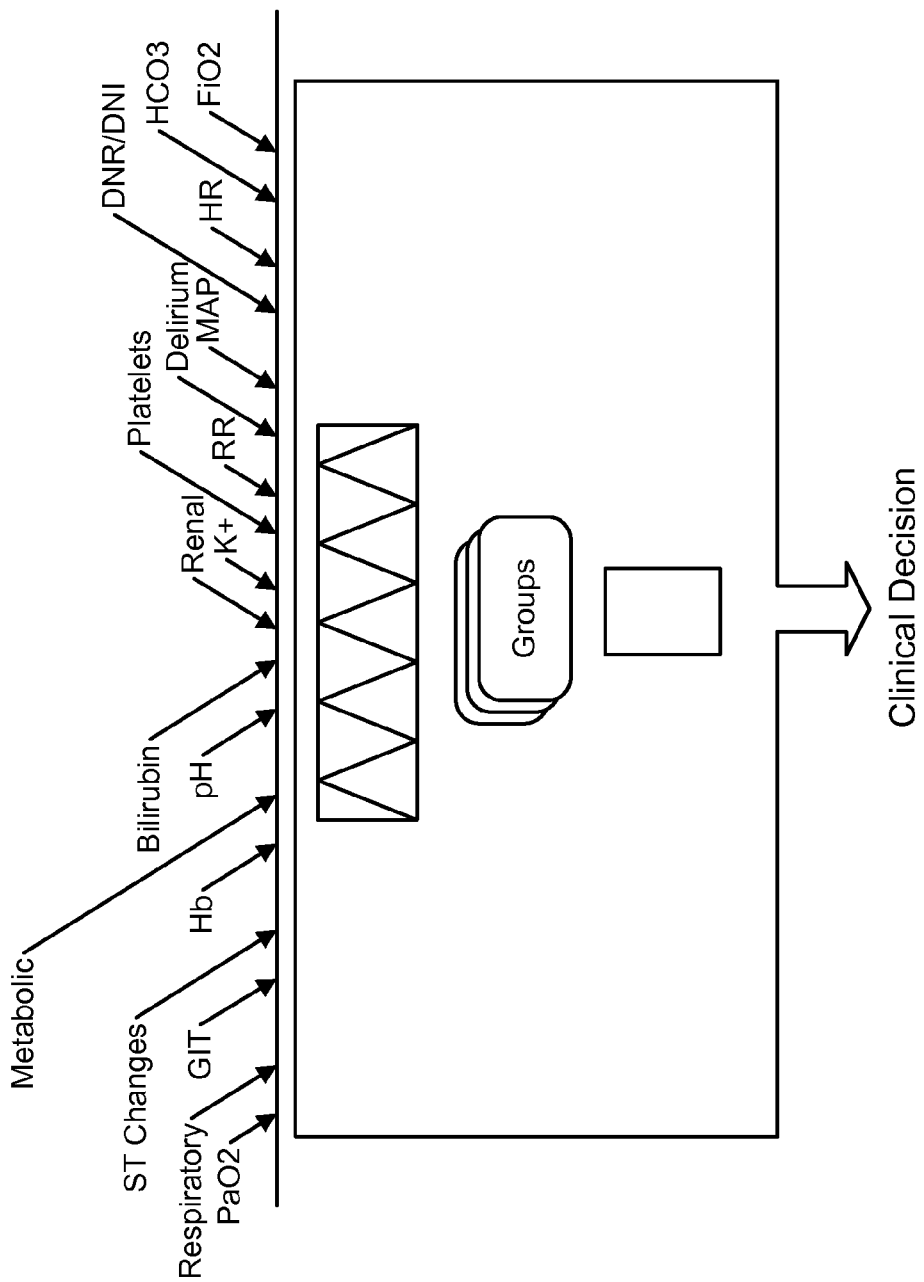
FIG. 1 is a conceptual flow diagram showing the processing of patient related ICU information into a clinical decision to aid the patient.

This document describes systems and techniques for identifying data that is most likely to lead to positive patient outcomes, and for presenting that data to caregivers in a manner that the caregivers can produce the positive outcomes. In one implementation, the techniques here involve acute warning and response valuation (AWARE), which may be used to increase the signal-to-noise ratio for data in a setting such as an ICU. The AWARE system screens or filters data that may be found throughout a healthcare system, from immediate information about a patient, such as blood pressure, to medical record information, to medical history information.

After the screening or filtering, the relevant data is bundled into discrete "information packages" which are then formatted and presented to a caregiver. Information packages contain the most relevant data and facilitate real time clinical decision making and care delivery. The AWARE interface gathers highly valued patient data into a single location and compartmentalizes that data into information packages so as to facilitate clinical decision making. In addition, the AWARE interface facilitates syndrome-related bundling of implementation by allowing physicians to order and track relevant investigations and treatments in real time at the bedside.

The AWARE system addresses a number of building blocks. First, the system uses data point utility in decision making (DUM) scores, whereby clinical data is allocated a score based on its frequency of use in medical decision making. DUM scores generally vary with clinical context, such as prior medical history and ICU syndrome development (e.g. sepsis). DUM scores can be used to screen data points for their likely relevance to clinical decision making. Once known, the DUM score is incorporated into an algorithm which defines when and how that data point is displayed to the physician.

The AWARE system correlates a number of components to each other. First, the system employs "clinical information packages," which are bundles of related data that are recognizable as such to an experienced physician. Such packages may be formed by applying heuristic rules generated by surveys of experienced caregivers or other observations of such caregivers. The surveys may seek to determine which data points the caregivers address most often when encountering a patient in a particular situation.

The packages can be organized by organ system, and the content can be informed by context-specific DUM scores. The main components of the package include: (1) clinical contextual information (medical background, admission diagnosis, acquired diagnosis); (2) current physiological status (heart rate, respiratory rate etc); (3) Current ICU supports (fluid and pressor requirements, ventilator requirements etc); (4) relevant investigation results (ECG, Hb etc.); (5) relevant investigations status; and (6) relevant interventions status.

Second, the AWARE system uses "medical context search," which searches, using key words, a patient's past medical history and problem list in the patient's electronic medical record. The past medical history defines one element of the clinical context in which data should be interpreted. Once detected, the system defines when and how those key words are presented to the physician.

Third, the AWARE system uses "organ failure awareness." Acute illness management centrally involves the recognition and treatment of organ failures. A system may screen for the development of organ failures and modify the content of clinical information packages accordingly. The detection of organ failures triggers modifications to the relevant clinical information packages. By expanding individual information packages in this fashion, the physician will have instant access to organ specific data and increased awareness of the most vulnerable organ systems in individual patients. Early recognition of such organ failures reduces the time to appropriate interventions and may alter patient outcomes.

Fourth, the AWARE system includes "ICU syndrome awareness." The early recognition and treatment of syndromes such as sepsis is associated with improved patient outcomes. Delayed recognition and treatment is associated with poor outcomes. A system may screen for the potential development of ICU syndromes such as shock and sepsis. The detection of such syndromes can trigger the display of information packages relevant to the differential diagnosis and treatment of that particular syndrome. By presenting data in this fashion, the physician or other caregiver is immediately alerted to the potential development of acute illness syndromes and can immediately implement appropriate therapies or interventions.

Fifth, the AWARE system includes "treatment implementation awareness." Once specific syndromes are identified, the status of each component of management of that syndrome can be displayed in the information package format.

Compliance with the relevant components of management can thus be displayed in real time. Once sepsis is diagnosed, for example, the status of relevant treatments (e.g., broad spectrum antibiotic administration, fluid resuscitation, pressor use), relevant investigations (e.g., blood cultures, SvO2, lactate, CBC/Hct, Type and screen), and relevant targets (e.g., MAP>65 mmHg, antibiotic admin. <1 hour, SvO2>70%) can be displayed in a Sepsis AWARE information package.

Sixth, the AWARE system provides for interacting with an AWARE interface in a number of ways. For example, physicians may perform ordering from within patient information packages by integrating the system with CPOE applications. The results of investigations that carry a high DUM score for a particular clinical syndrome will be displayed within information packages. The status of the investigation will be indicated to the physician. The status of investigations will include: not ordered, ordered but not done, done not available, and available. Evidence-based interventions will also be included in the syndrome specific information package. The status of the intervention will include: not ordered, ordered not completed, and completed.

The physician may also be given the opportunity to trigger the recognition of syndromes or organ failures by inputting diagnosis directly into the bedside display. In this way, the clinician can trigger the display of all relevant syndrome-specific information packages. By allowing a physician to interact in this way, the utility of the AWARE display may be improved for the physician.

FIG. 1 is a conceptual flow diagram showing the processing of patient-related ICU information into a clinical decision to aid the patient. At the top of the figure, a large plurality of data points are shown entering a box that represents a process for preparing data for human clinical decision making. The data points include a variety of data types, including real time information being read from the patient, such as oxygen levels, heart rate, and other similar factors. In addition, the data points can include information from an electronic medical records system whose data is stored separate and distinct from the real time data, and can include factors such as laboratory results for a patient. In addition, the data points can include more distant data, such as data form the patient's medical history, which may be obtained from the electronic medical record system or from another source. The real time data, in one example, may be obtained from a system that is local in the patient's room, while the electronic medical record data may be obtained from a central system in a hospital facility, including from a centrally-located data stored that is accessed over a network that can include the internet (using, for example, well-known secure communication techniques).

The first component in the conceptual box is a filter. The filter may serve to extract, from the large plurality of data points, particular data points that are needed in the system. The filter may be provided with particular fields in a system that are to be extracted from the various data stores (e.g., local real time data stores, electronic medical record data store, etc.), and then request values for the particular patient in those fields. The fields may be identified by heuristic rules that may implement preferences that have been determined by surveys or other studies of experienced caregivers. For example, experienced caregivers may be asked to identify the data points that they consider during various patient care scenarios, and the data points for those scenarios may be extracted using the filter. The filter may then save the extracted values in its own data store, and may update the extracted values periodically. The periodicity may vary based on the data store type, with updates from a real time data store occurring, for example, on the order of every second, and updates from an electronic medical record occurring on the order of minutes or more.

The filter may also be programmed to look for matches to certain values in the data store. In such a situation, the system may be more flexible in that it may address multiple different systems without detailed programming to match the filter to the particular system. For example, the filter may extract electronic medical record data for a certain patient based on a label for a field, without having to be previously programmed with the actual location for that field.

By this process, the filter may extract a subset of all the available data points in a system of stored patient data, according to data points that have been determined to be of most interest to caregivers in a particular field (e.g., ICU, etc.), at a particular job title level (e.g., attending physician, ICU nurse, etc.), and under a particular set of circumstances (e.g., patient undergoing organ failure). The extraction process may narrow the information for presentation to a level that is manageable and understandable to a typical caregiver.

Shown below the filter are a number of groups. The groups represent collections of data points that share a common characteristic. For example, the groups can be arranged according to organ or organ function. Each member of a group can represent a particular patient values (e.g., pH, pulse rate, etc.) or a derivative value that is determined from one or more patient values. The members can also include indications, such as indications that extreme values should be displayed in an emphasized manner, such as via a sound, a color (e.g., red for critical), blinking, a larger font, or a bold font. Particular examples of groupings or groups are discussed below.

The bottom component of the box is a presentation manager. The presentation manager provides for the manner in which the groups and data points within the groups are to be displayed. The presentation manager, for example, may determine textual labels and fonts for particular data point values. The presentation manager may also determine the relative positioning of groups and elements on a page, and the positioning between pages where the system generates a multi-page interface. In addition, the presentation manager may generate icons or other graphics to present certain values, such as data point values. For example, a cardiac grouping may be represented by an icon of a heart, while a pulmonary grouping may be represented by an icon of a patient's lungs. Other graphical information, such as traces of graphs may also be employed, and may be computed by a system from other values.

The output of the box may be a graphical display on a video monitor in the proximity of a patient, which a caregiver may review, and preferably may review quickly and effectively because an appropriate subset of data points is displayed, and is grouped and formatted in a convenient manner for the caregiver. Such output may readily lead to a caregiver making a quick and accurate clinical decision, such as by changing the medication or other therapy provided to a patient, or by ordering that a particular procedure or test be performed on a patient.

Figure 2:
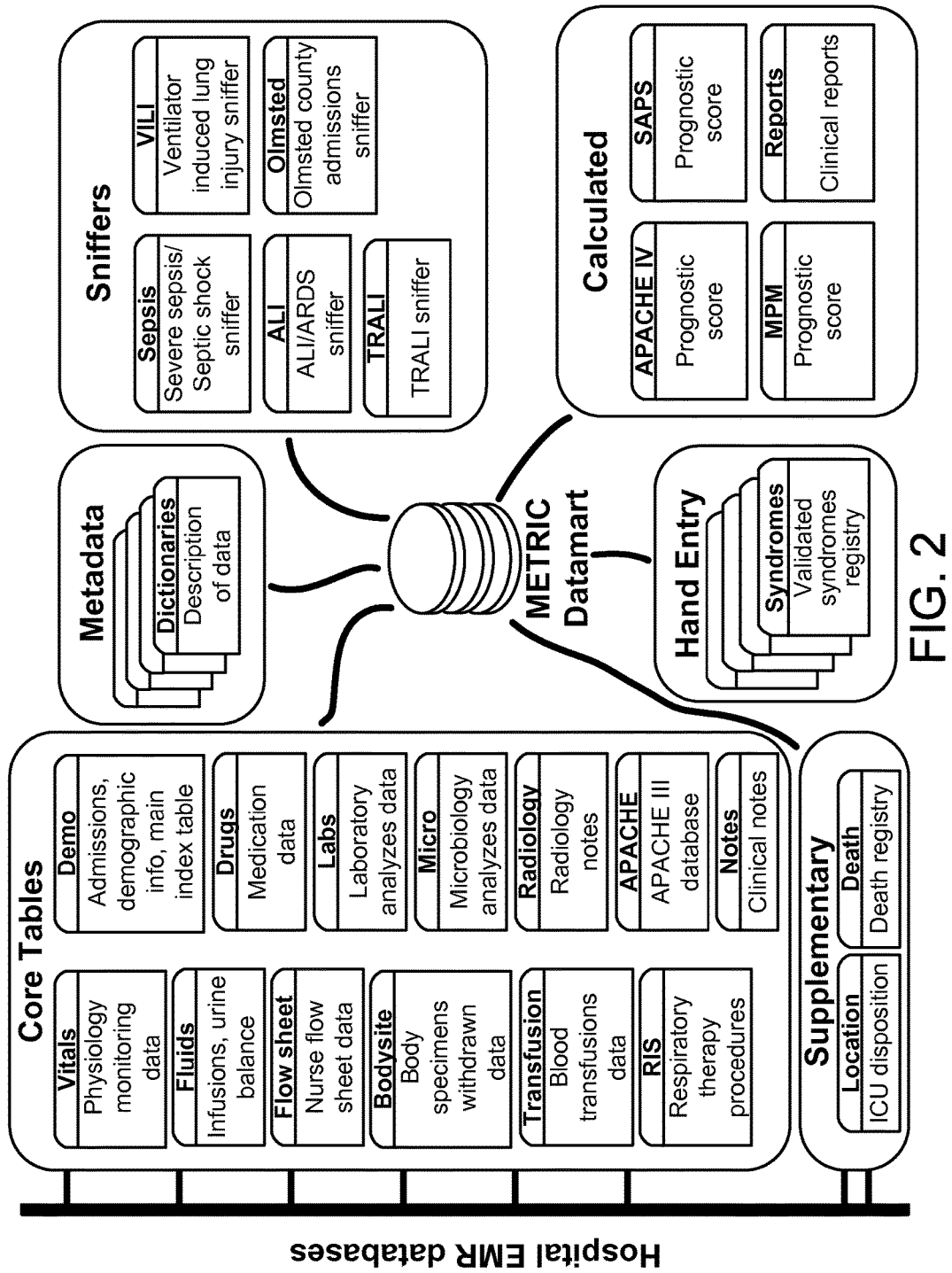
FIG. 2 is a block diagram showing various patient-related data sources.

FIG. 2 is a block diagram showing various patient-related data sources. Each source may be in a separate and independent data stores. Sniffers may include components that are training to extract data from other sources, such as particular admissions files, and other locations. Metadata includes data stores containing data about data in the rest of the system, such as dictionaries that describe the data that is available in a system.

Such dictionaries may be helpful to a caregiver who is designing a custom presentation for a monitor (where the custom presentation may be triggered whenever the caregiver's presence is detected near a monitor, as discussed with respect to FIG. 9 below). For example, caregivers may use touch screens and key board inputs to select data points that they prefer to see in particular situations, and may then drag groups for those indicators around a display using the touch screen input, and may drag data points around inside each group, so as to produce a display that works best for the particular caregiver. A caregiver may also set up their screens more quickly by entering an identifier for another caregiver whose layouts they like, and those layouts may be applied automatically to the screens for the first caregiver.

Calculated values are stored in another data store or stores. The values may take a variety of forms, including clinical reports on a patient. Also, hand entered data may also be accessed, and a variety of electronic medical record data may be separately accessed. The medical record data may include lab results, clinical notes, nurse flow sheet data, and the like.

Figure 3B:
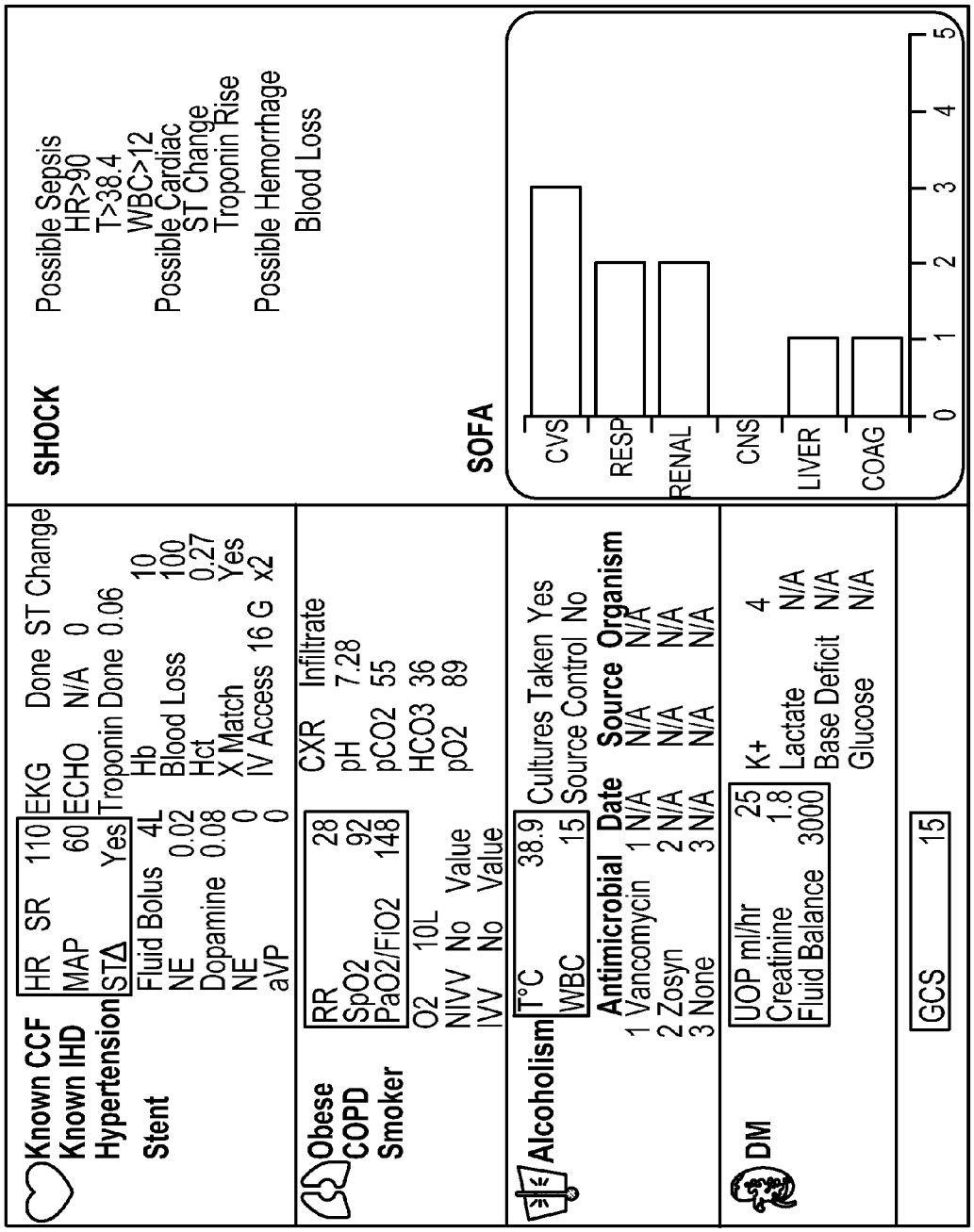

FIGS. 3A to 3H show example displays that may be shown to caregivers in an ICU setting. FIG. 3A shows displays for multiple patients (which may be displayed, for example, at a central station) and FIG. 3B shows a display for a particular patient. The display in this example is divided into three zones: (1) clinical information packages along the left side; (2) a syndrome detection advisory and physician interaction panel in the upper right, and (3) an organ status summary display in the lower right.

In the left side of each of the information packages display, an organ identifier is shown (e.g., heart, lung, kidney, etc.). To the right of that is organ specific clinical contextual data, such as whether the patient has a stent, hypertension, or other similar status. To the right of and at the top of each package are shown current organ physiological status, such as heart rate and MAP for cardiac packages. Key data in each of these packages are always displayed if available.

Below the current organ physiological status is current organ support status such as Norepinephrine (NE) and dopamine levels. This area is displayed when organ failure is detected. To the right is the relevant (high DUM score) organ associated data, including data point identifier, status of Investigation/Intervention, and data point value. This area is displayed when organ failure or ICU syndrome is detected. The content of this area is determined by the context and is informed by the DUM score database. The physician may interact with this segment of the screen and order investigations or interventions directly from here.

Figure 3C:
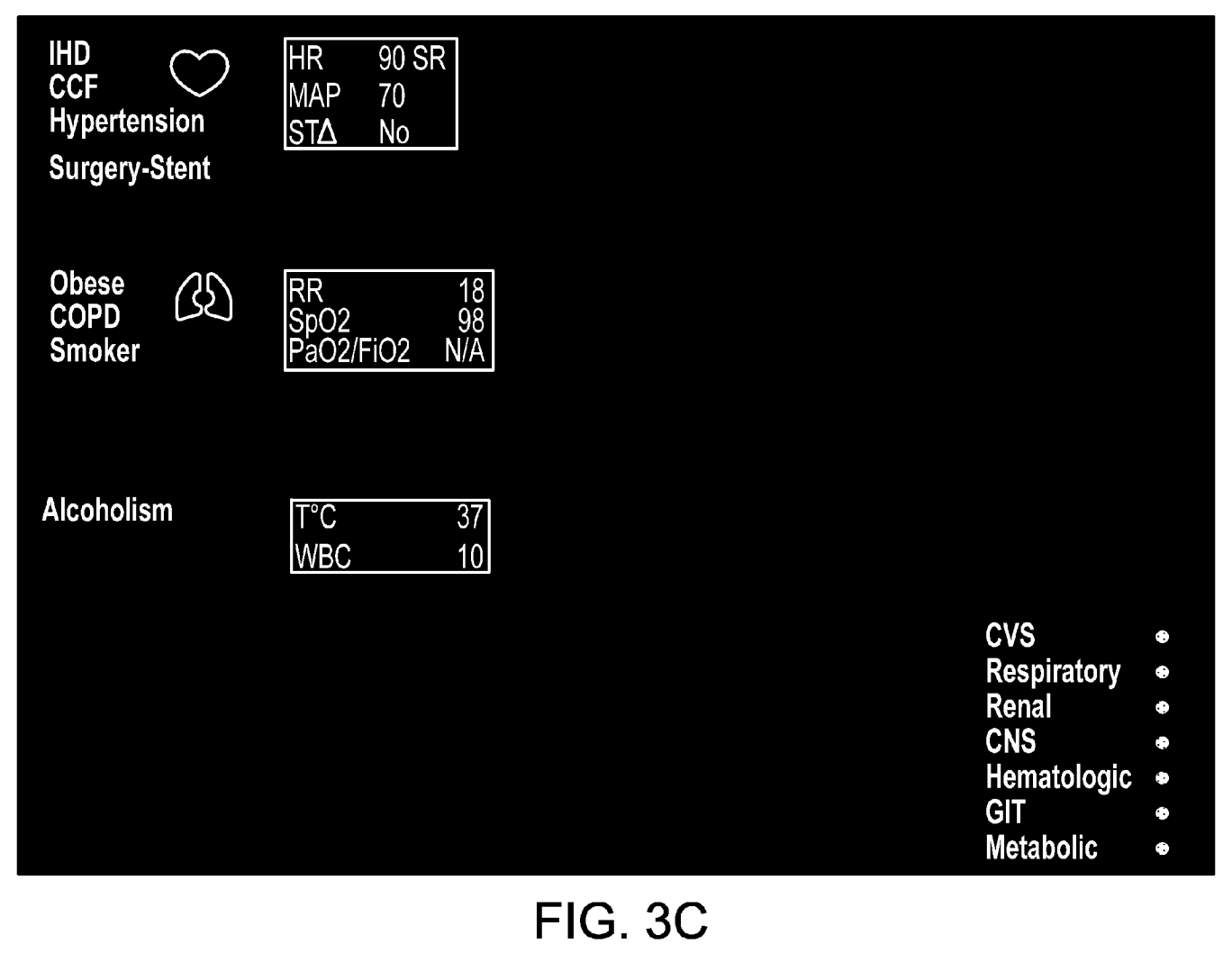
Figure 3D:
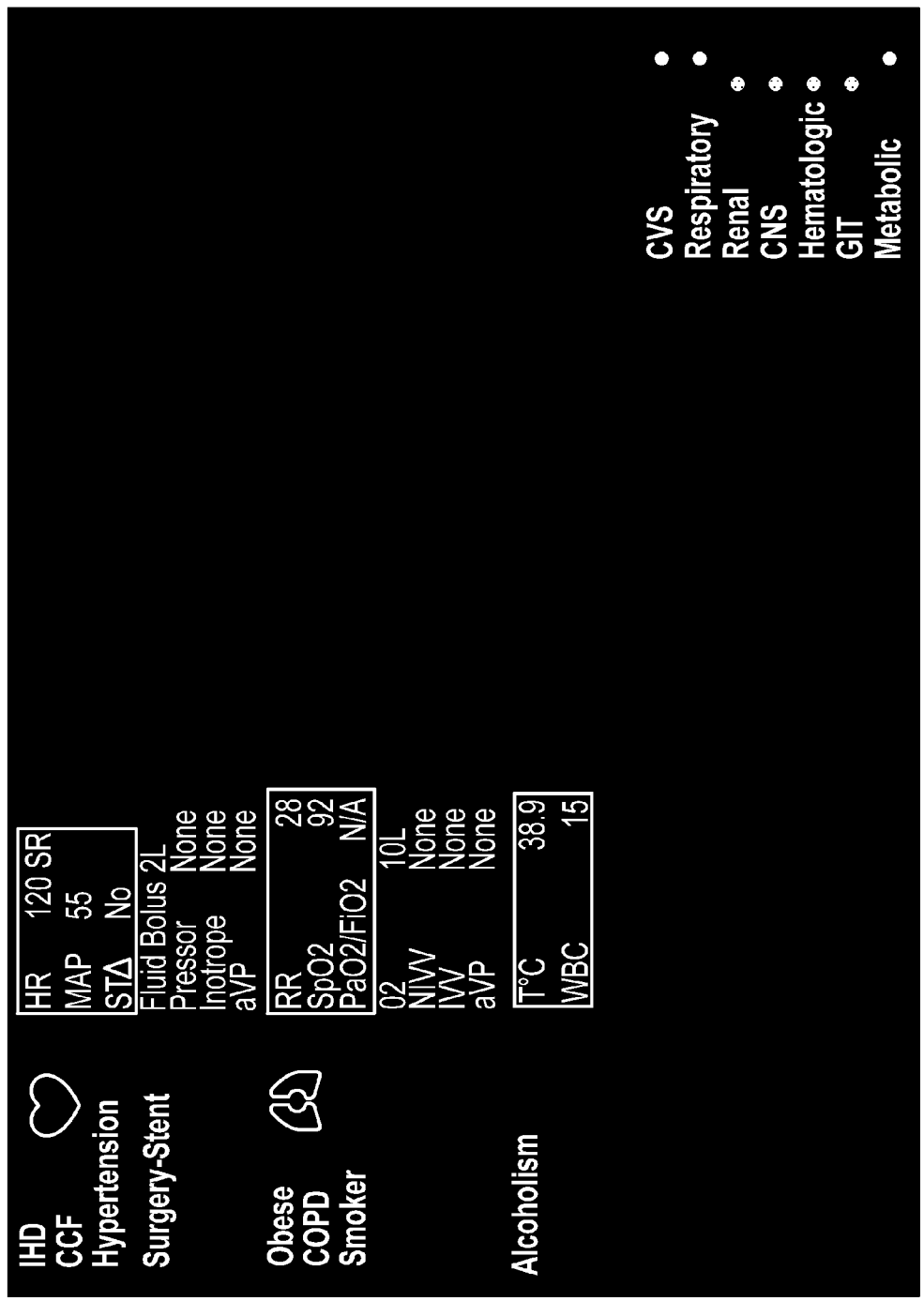
Figure 3E:
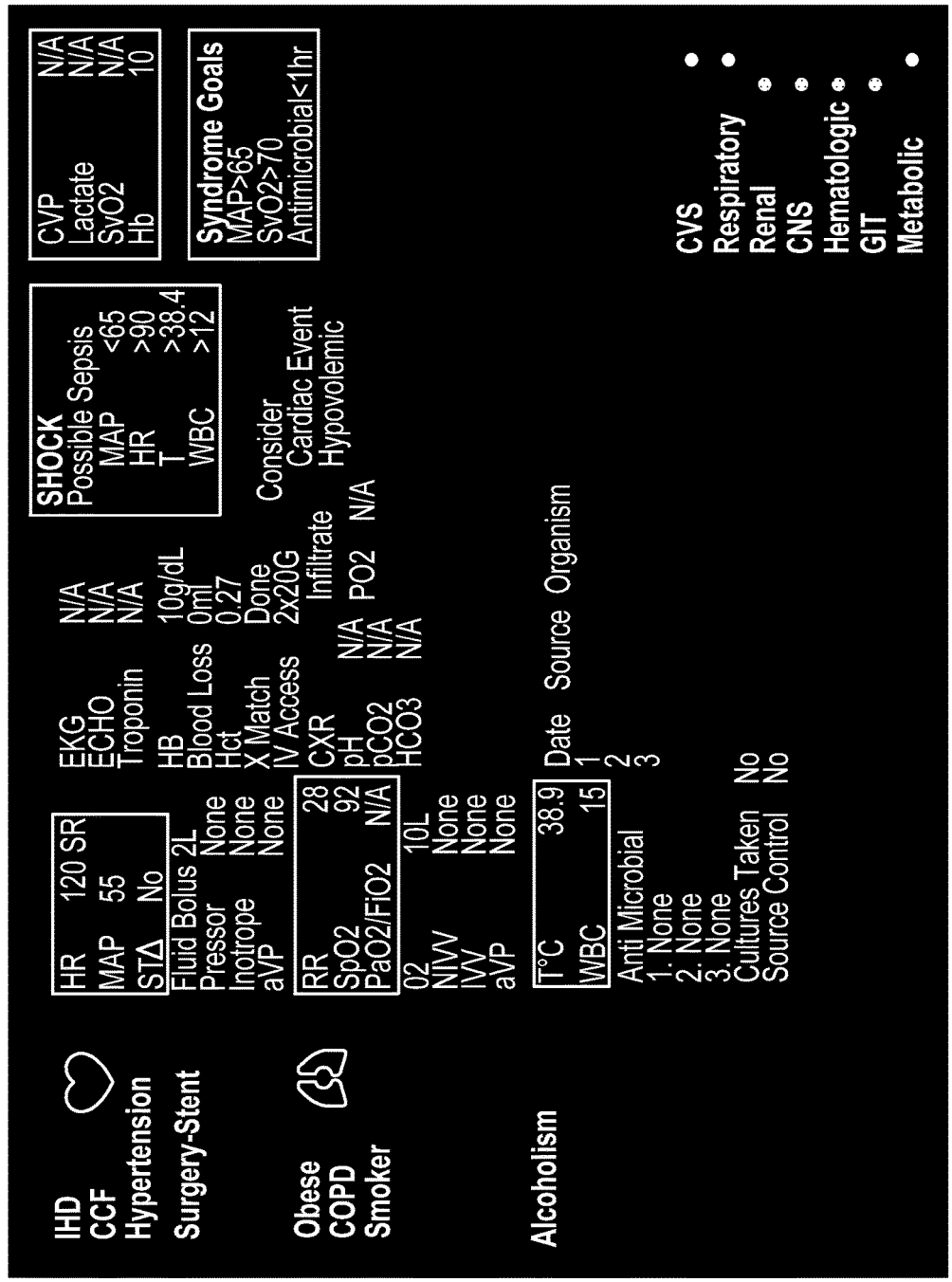

In the lower right corner of the screen, an organ status summary display is provided. This section displays a summary of the current organ status. In this version, the organ status is displayed based on SOFA scores. This is updated every 15 minutes in the present example. An XY plot of SOFA score (Y-axis) against Time (X-axis) can be accessed from this segment of the display. Such accessibility can enable the physician to display the organ trajectory over time FIGS. 3C to 3F shows a progression of displays that may be generated for a particular patient. In FIG. 3C, three areas are displayed and all factors are relatively normal. The patient presents a number of challenges, in terms of hypertension, a stent, obesity, and a history of smoking. In FIG. 3D, several areas and data points have been highlighted to emphasize a changed that has occurred in the patient and the data points. Also, in the lower right corner of the display, the particular groups of information being tracked by the system are shown as having changed status in some instances. In FIG. 3E, the patient is shown as being in shock. Such a display may be generated automatically, or by input from a caregiver, such as the caregiver recognizing that the patient is in shock, and providing a command to the system so that information regarding parameters associated with shock may be displayed. In this display, syndrome detection advisory and provisions for physician interaction are shown in the upper right corner of the display. Such a display may be similar to a display like that shown in FIG. 3B. The upper right area, in this example, is active only when a critical illness syndrome is detected. The display includes an advisory as to which primary ("SHOCK") and secondary ("Possible Sepsis") syndrome or syndromes have been detected. In addition, it contains a description of which component of the syndrome has been detected as being present (e.g., "HR>90"). The physician may trigger the activation of this section by inputting a diagnosis into the display. This will result in a modification to the AWARE display which presents syndrome specific data that has high DUM scores.

Figure 3F:
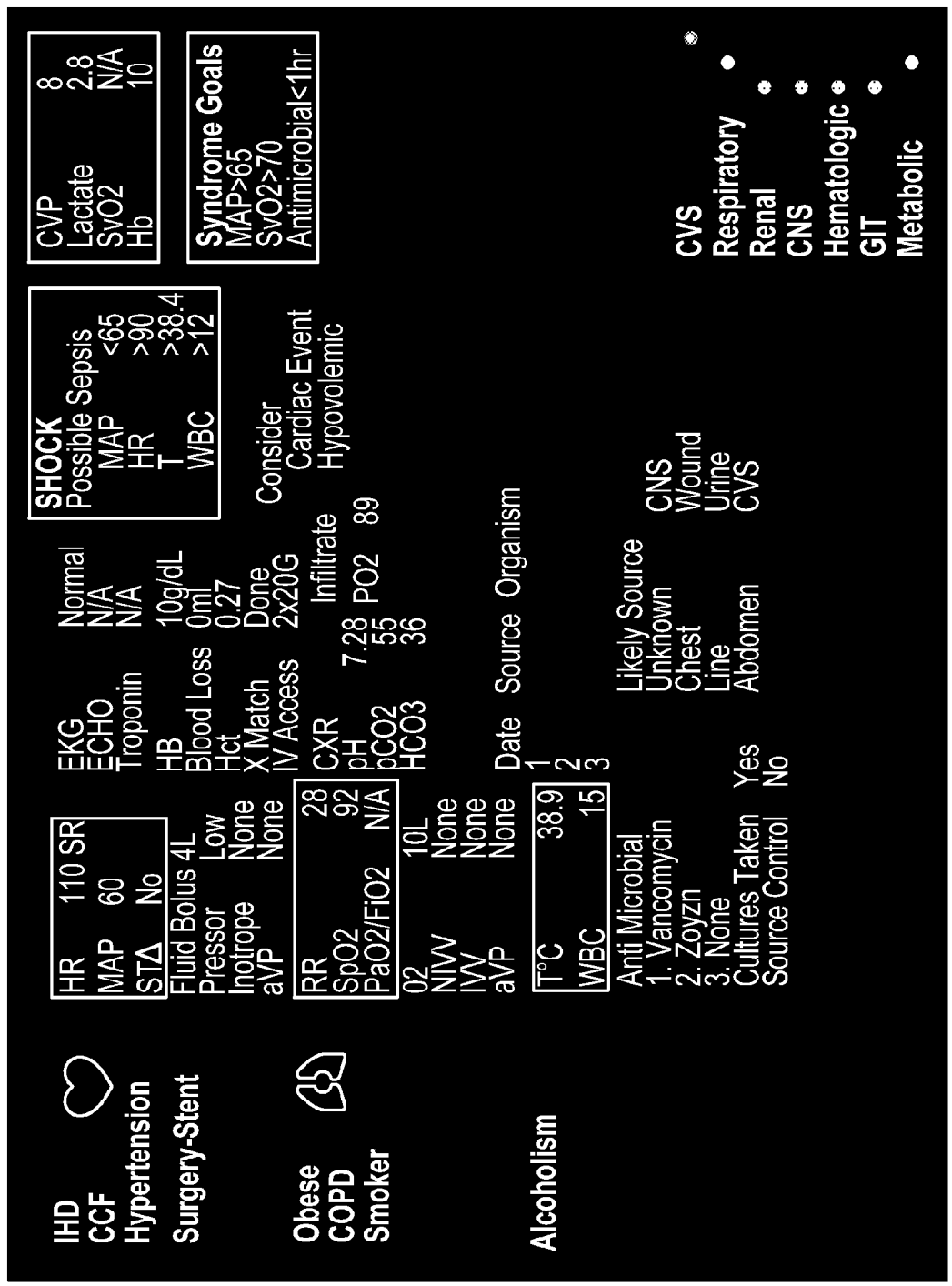

FIG. 3F shows values for further progress with the patient during the episode of shock. The status for CVS in the lower right has now shifted into a third status area.

Figure 3G:
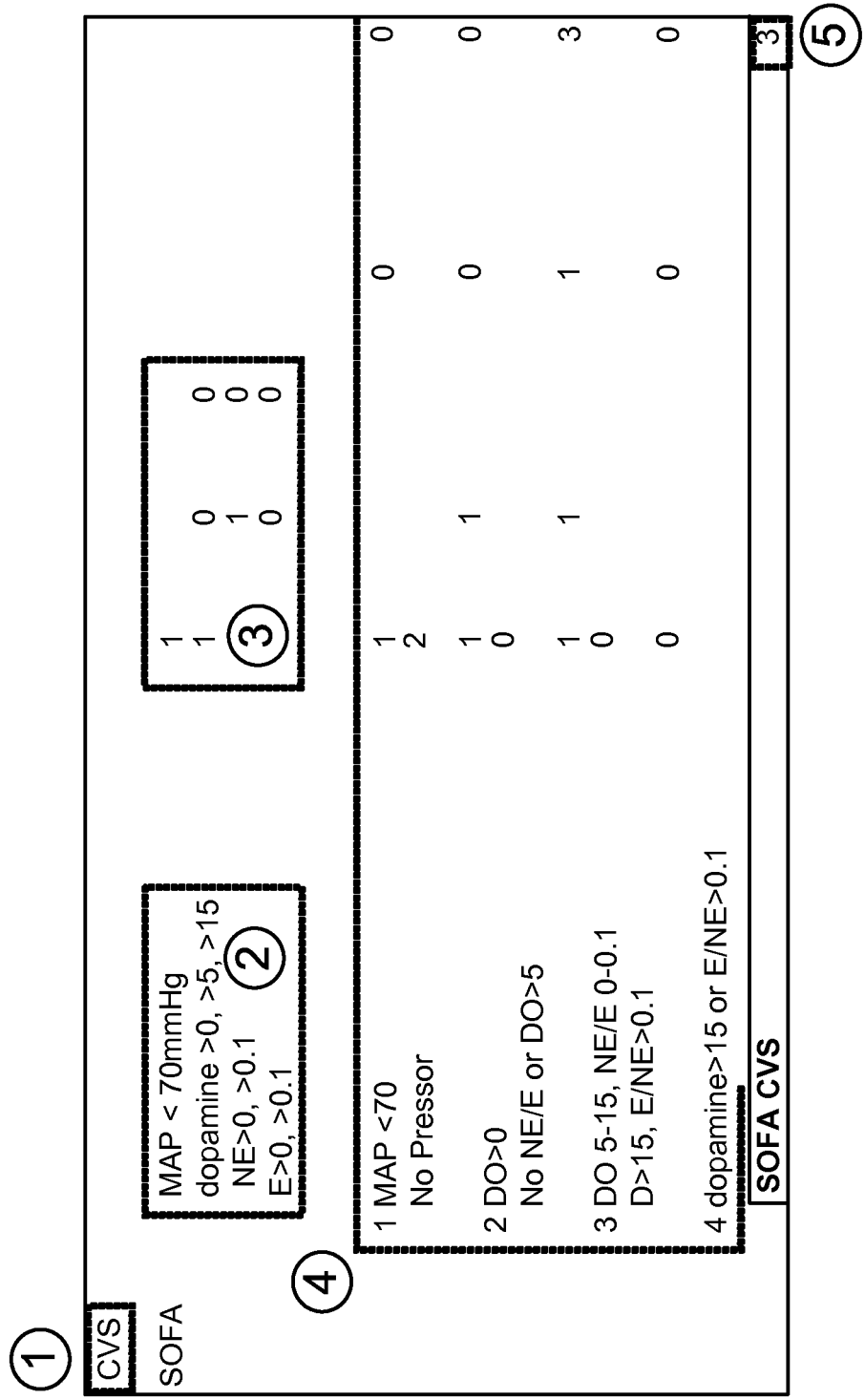

FIG. 3G shows an organ failure detection screen area. Zone 1 is an organ identifier. Zone 2 shows organ failure detection rules (using SOFA score). Zone 3 shows organ failure detection status from a DUM database. Zone 4 shows an organ failure score calculation, and zone 5 shows an organ failure score (from SOFA scoring system).

FIG. 3H shows a syndrome detection screen area. Zone 1 shows a primary syndrome detected, while zone 2 shows secondary syndrome identifiers. Zone 3 shows key components for recognition of the syndrome. Zone 4 shows: (a) detection status (1=present, 0=not present); (b) secondary rule used when combination of triggers are required to activate a syndrome advisory. Zone 5 shows the value to be displayed in association with a syndrome advisory. This notifies a physician of AWARE detection of specific components of a syndrome. And zone 6 shows a syndrome advisory. This notifies the physician which of the potential causes of the primary syndrome have been detected.

Figure 4:
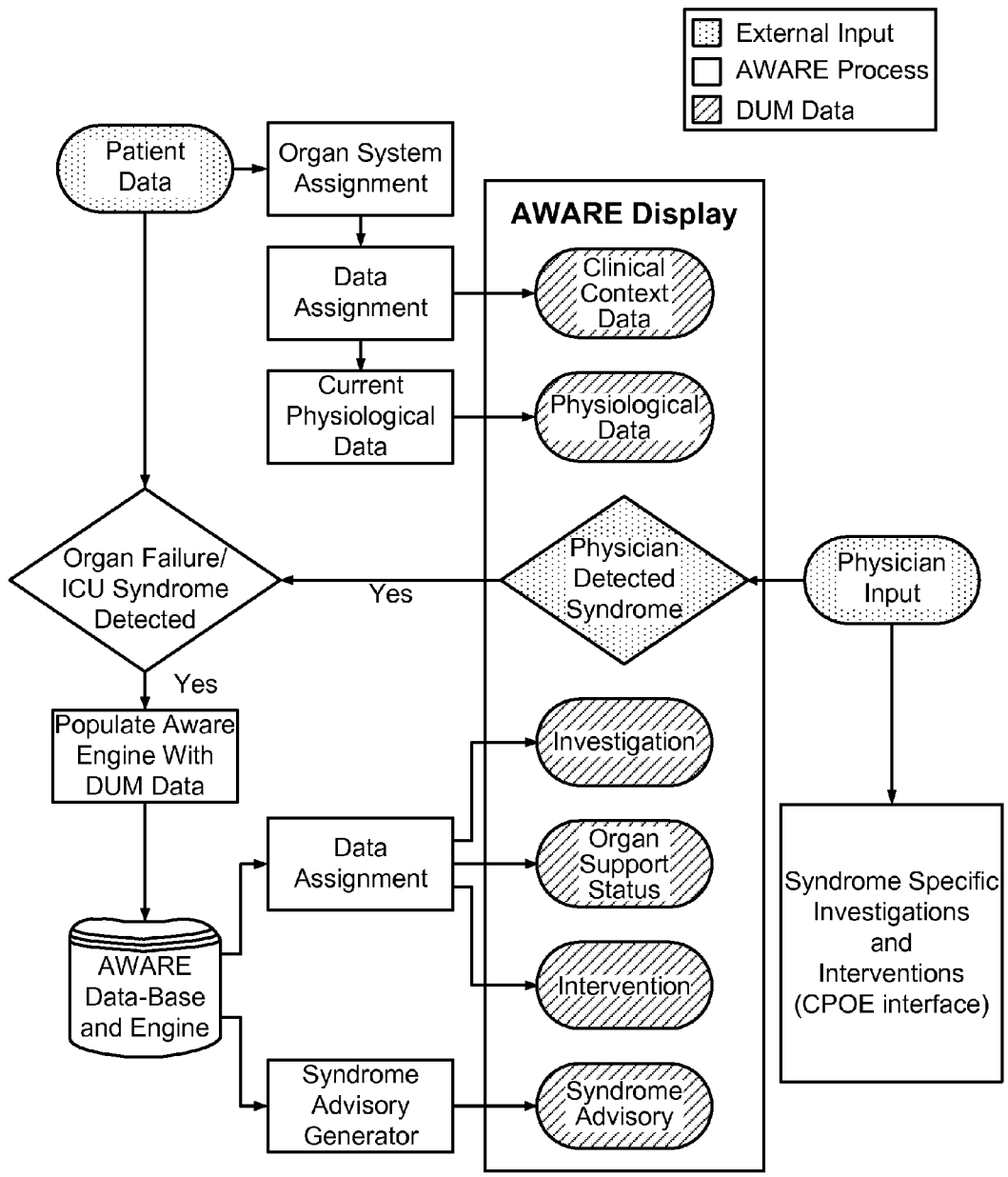
FIG. 4 is a flow chart showing actions for processing and presenting patient-related ICU information.

FIG. 4 is a flow chart showing actions for processing and presenting patient-related ICU information. At a starting point, patient data is received. In ordinary operation, organ systems may be assigned for display on a patient monitor, data for the patient can be assigned to groups formed in association with those systems, and current physiological data for the patient may be obtained, such as by monitoring equipment proximate to the patient. Such data may then be displayed.

At a decision box, either organ failure or a syndrome are detected, either automatically, or from a physician detecting a syndrome and entering that observation into the system. The system engine may then be populated with data regarding data points determined by DUM to be relevant for the particular patient status. Data assignments may then be made, and a system display may interact with a physician regarding follow-up investigations, organ support status, and intervention. Also, a syndrome advisory generator may provide for a display of a syndrome advisory to the caregiver. The caregiver may provide input back to the system with respect to things like syndrome specific interventions and investigations, such as via a CPOE interface to the system.

Certain surveys may be used to identify the data points that should be displayed to physicians for maximum effectiveness of a patient monitoring system. For example, in a survey of 34 data points available to physicians in an ICU, a median (IQR) of 11 (8-18) data points were used by at least one of 60 surveyed physicians. Some data points were used more frequently than others. (Chi-square 232, DF 33, p<0.0001). The following were in the top quartile of utilization: SpO2, RR, HR, MAP, DNR/DNI status, CXR changes, FiO2, respiratory support level and fluid balance. Data points included in the bottom quartile included PaCO2, bilirubin, HCO3, glucose and base deficit.

FIG. 5 shows data from such a survey of physicians. Fifteen attending intensivists were surveyed to judge which of a 35 point data set were most clinically useful. The physicians were asked to agree or disagree with the statement "this data point is useful when forming medical judgments about new ICU admissions." Each data point was scored using a Liked scale: 1 (strongly disagree) to 5 (strongly agree). This score was termed the "data impact on medical judgment score" (DIM). Physician-provided DIM scores for all data points had a median (IQR) value of 4.41 (3.92-4.67). When DIM scores were categorized by data-point or physician significant differences were found using Kruskal-Wallis test p<0.0001: Kruskal-Wallis statistic 142 and 106 respectively. High mean DIM score suggests that caregivers common use the points in the formation of medical judgments in an ICU. Variance between DIM data-point scores suggests that some of the included data points are less generally useful than others and that this is significantly physician dependent.

This dataset was presented to all physician (attending and non-attending) members of the admitting ICU team between 1.5-3 hours of a new patient arrival. Subjects were asked to "identify those data points which you considered relevant for the diagnosis and management" of the newly admitted patient. The number of data points (out of the 33 present on the clinical study questionnaire) used in decision making per physician-patient interaction were calculated. The frequency with which individual data points were used by physicians in decision making was calculated as a fraction of all captured physician-patient interactions. This score was termed the "data utilization in medical decision making score" (DUM). The methodology utilized to profile users' data needs is applicable to any provider-task combination.

The top graph in FIG. 5 shows average physician ratings regarding the relevance of a number of data points that might be relevant to monitoring and acting on the condition of a patient. The bottom left graph shows the number of data points that were used to treat any one admitted patient. As indicated, 218 physician questionnaires were examined to determine the frequency of data utilization per admission. Both attending and non-attending physician responses were included. The median (IQR) number of data points utilized were 9 (5-15). As shown, in almost all cases, the number of data points used per admission were in the single digits to teens.

The lower right graph introduces the concept of a Data Utilization in Medical decision making (DUM) score. The frequency distribution of DUM scores for 33 included admission data points are demonstrated in the graph. DUM scores for each data point were calculated from the 218 physician-patient admission interactions as follows: Sum of times data point utilized by physican/218. The median (IQR) of DUM scores were 0.29 (0.21-0.38). The identification, by DUM score, of data points which substantially contribute to medical decision making can be an important first step in the redesign and rationalization of ICU data presentation formats.

Figure 6:
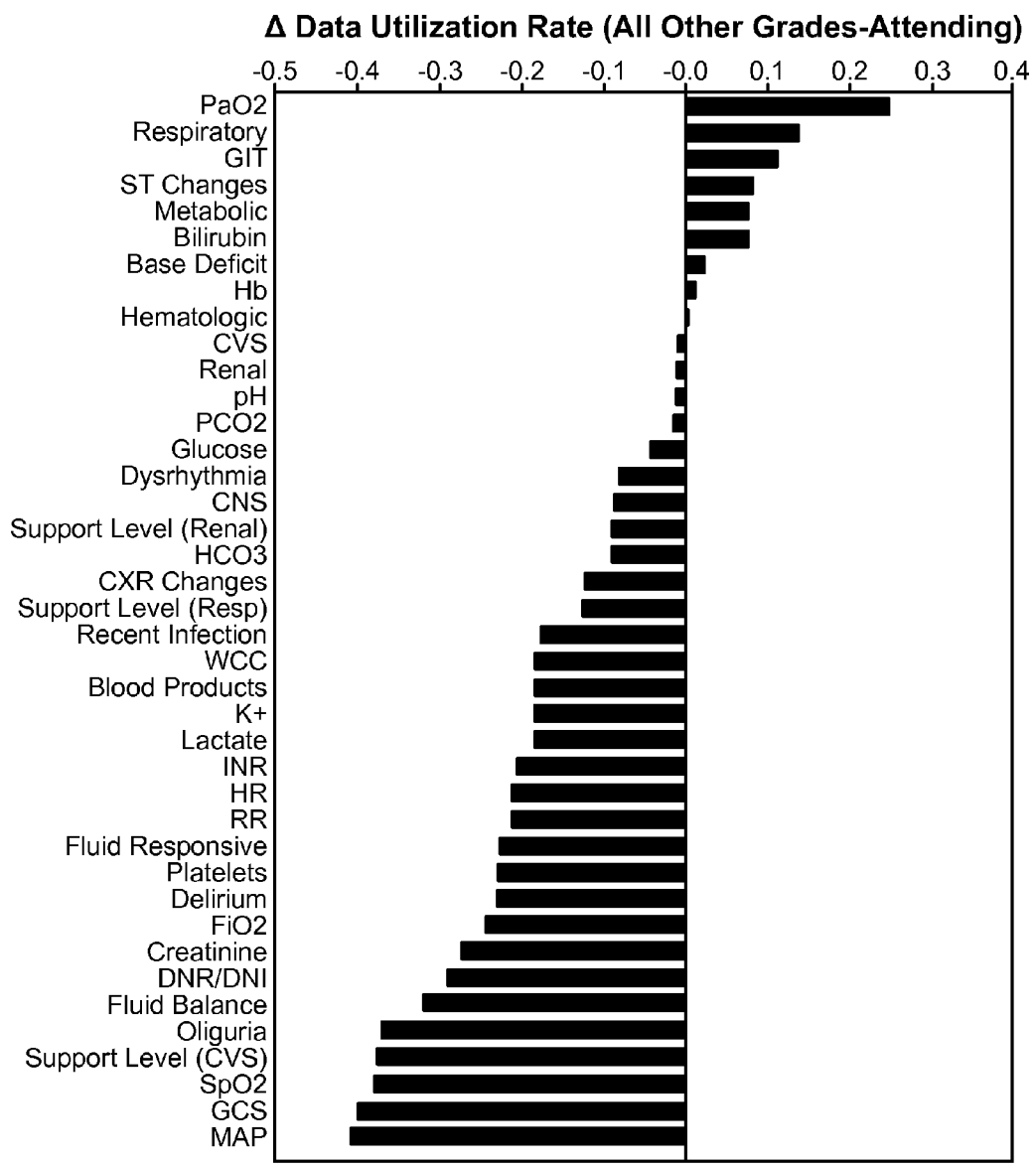
FIG. 6 is a graph showing variance between attending physicians and other caregivers in terms of preference for particular ICU-related data points.

Studies also indicate differences in the usage of data points to which physicians of varying experience or skill levels. FIG. 6 is a graph showing differences between attending physicians and all other grades of physicians in terms of the data points to which they refer. To obtain the data for the graph, a 34-point data-set was presented to all physician members of an admitting ICU team within 2 hours of a new patient's arrival. Physicians were asked to identify data points they considered relevant for their initial diagnosis and management. Comparisons between attending and non-attending physician data utilization were made. Responses relating to 56 physician-patient interactions were collected. Of 34 data points, a median (IQR) of 13.5 (8-17) and 6 (3-9.75) were utilized by consultants (n=14) and all other grades (n=40), respectively (Chi Square 6.7, p<0.001). Matched pair analysis of individual data point utilization rates demonstrated a mean difference (95% CI) of −0.17 (−0.11 to −0.22), p<0.0001.

The graph thus shows some significant differences in data point frequency-of-utilization in admission decision making processes between physician grades in the ICU. Attendings use a greater number of data points and do not place the same value on some laboratory data compared to other grades of physician. These findings suggest that ICU experts and non-experts do not share a view on the decision making value of individual patient data points. Identification of these differences may contribute to the development of a rational patient-data presentation format for use in the ICU. In addition, by characterizing expert defined high value data sets, physicians in training may gain insights into model decision making processes and contribute positively to their acquisition.

FIG. 7 shows an example screen shot, or display, of a patient monitoring interactive checklist. The particular display shown here is exemplary only, and particular arrangements, display decisions, and user interactions should not be treated as limiting.

The checklist in the display of the figure presents a user interface that is populated with information about a patient and the patient's condition that is automatically pulled from various sources, such as the patient data 240 data store and data aggregation unit 228 of FIG. 2B, among others. The interface may be presented on a touch screen device so that a caregiver can see the patient's condition and default settings for the system, and may choose to leave the settings alone or to change them. Certain of the settings may affect the notification functionality of the system discussed above. Also, certain entries on the interface may be written to the patient's chart and stored as part of the patient's medical record. The association between the device that provides the interface and the particular patient may be made using a variety of known techniques, such as a caregiver log in (which may include biometric identification) and identification of the patient, where the state of the system may be maintained (i.e., the patient or patients who are associated with a terminal may be remembered by the system so that a caregiver may quickly access their data).

The display is broken visually into several sections to better guide a caregiver's attention as they review data from the display and perhaps enter data into the system, such as by directly onto a touch screen layer over the display. For example, at the top of the display is a greeting that indicates the date and a patient name, along with introductory text indicating the values below related to information that has been detected by the system.

Inside a visual box are three sections—a first section relating to ventilation for the patient (here, a Mr. Jones), a second section relating to intravenous (IV) treatment being provided to the patient, and a third relating to certain real time key conditions of the patient. Label 701 is a heading for the ventilated section, and is color coded to indicator a current status of the patient. If the ventilator mode is "no ventilator" (" ") the indicator is colored red, or "Ventilator" (e.g. "BIPAP") then it is green. As a secondary rule, if the indicator is green, then the ventilator checklist is displayed below the label (as is shown here). The displayed status is the most recent status for the patient, and the status, in a particular example, is updated every two hours. Label 702 represents Head of Bed (HOB), which is also color-coded— green if the HOB was 30 degrees or greater in the last 24 hours, or else red. Such colors may be shown in the text of the label itself and/or in indicator dots 714. If the color is green, then the system determines the percentage of time the HOB exceeded 30 degrees in the prior 24 hours. The displayed value is the most recent value, and the value is updated every four hours.

Label 703 represents the patient's ulcer prophylaxis, which represents (via searching a patient's electronic records) whether the patient has received Omeprazole, Ranitidine, Lansoprazole, Famotidine, Pantoprazole, Cimetidine, Esomeprazole, Nizatidine, or Rabeprazole. If they have received any of these agents, the display shows the dosage and agent name, the administration schedule and administration schedule. If none of these agents is found, then the display says "NONE." The displayed values are from the last patient administration, and the values are updated every 24 hours. As shown, the data may be arranged in a template to provide for a natural language display rather than simply labels with data. Also, indicator 715 shows green if any relevant agents have been administered in the prior 24 hours, and red otherwise.

Label 704 represents deep venous thrombosis (DVT) prophylaxis, where the patient's records are searched for the presence of, by Boolean rule (Heparin OR Argatroban SC/SQ or IVI OR enoxaparin and SC/SQ OR dalteparin and SC/SQ AND part string 'SCD' (where SCD=sequential compression device for DVT prophylaxis) from a patient database. Again, any detected agent is displayed, along with the dose, administration schedule, administration time, and SCD. And again, the display may be in a natural language form, may show the last administration for the patient, and may be updated every 24 hours. In addition, indicator 715 shows green if any relevant agents have been administered in the prior 12 hours, and red otherwise.

Label 705 represents whether the patient is receiving sedation. To make such a determination, the system searches intravenous infusion (IVI) for agents that are listed in CNS (Central Nervous System) support rules. If an active agent is detected, (any sedative IVI drug running in the past 4 hours), the display shows the agent type and dose (e.g., in mcg/kg/min) and if no such agent is found, the display states "No IV sedation detected in past 4 hours". However, if a sedative agent is detected, then the display states "AGENT X discontinued at T=time." This label is displayed actively (and for agents discontinued in last 24 hours), and is updated every 4 hours. An indicator of sedative or aggitative state is given in the form of Richmond Agitation Sedation Score (RASS). The checkbox item (Selection 717), is predetermined as being appropriate (green) or inappropriate (red) by a secondary algorithm which combines data required for decision making. If a user disagrees with the generated result, they may select an alternative by any number of interactive gestures (click, point, touch).

Label 706 represents whether the patient has received a break from sedation, where if an active agent has been running for more than 24 hours, the system determines if there were any breaks greater than one hour in that time. If the agent has been running less than 24 hours, such a statement can be displayed, whereas if it has been running for more than 24 hours with no detected breaks, the display may state "No break in AGENT X detected in past 24 hours." Under a secondary rule, if a break is detected, then the display indicates the hours for the break start time and break end time. The display may be active and up-to-date, and may be updated regularly.

Label 707 represents whether the ventilator order is current—i.e., whether an appropriate caregiver has ordered the use of a ventilator on the patient within a prior time period that is consistent with normal standards of care. In this area, at least four values can be displayed. The Mode indicates the mode of ventilation that is being delivered (here, IMV, for intermittent mandatory ventilation). The Rate represents the number of inhalation and exhalation cycles per minute. The total volume (TV) is also shown in terms of ml per kg, where the patient's weight is obtained from electronic medical records. The total volume is computed as TV=TV/PBW (predicted body weight) ml/kg. If the patient is a male, then PBW=50+0.91*(height (cm)−152.4). If the patient is a female, then PBW=45.5+0.91*(height (cm)−152.4). The positive end-expiratory pressure (PEEP) is also shown, and is expressed in terms of cm of pressure. The checkbox item (Selection 718), is predetermined as being appropriate (green) or inappropriate (red) by a secondary algorithm which combines data required for decision making. If a user disagrees with the generated result, they may select an alternative by any number of interactive gestures (click, point, touch).

Next, a question is posed regarding a respiratory weaning assessment. If the caregiver makes a positive selection at 719, the system may gather data regarding the patient's medical history and respirator operation for the patient, and may determine whether the patient is breathing sufficiently on their own so that they could be slowly weaned off the respirator.

Label 709 indicates a zone of the display in which the system indicates whether any central IVI devices have been detected for the patient. The information is displayed if any central venous line (CVL) is detected, and a corresponding text label is lit. The names, sites, and times of insertion for each of the IV's are also shown, and selection 720 shows red or green depending on how long it has been since the IV insertion.

Label 710 provides a name of the particular IV while label 711 indicates the site on the patient's body where the IV placed, and label 712 indicates the insertion date for the particular IV. Finally, label 713 represents the site condition (clean, red, inflamed, pus). Selection 718—Using the information provided in 710-713, a determination may be made (algorithm or provider) as to whether an individual CVL is necessary for ongoing care (green) or should be removed (red). The selection of red generates a "remove this line" order. The selection of Green generates a "necessary for ongoing care" order. The output of this section is transmitted to a reporting database and is used by the hospital administration to generate reports for local, state and national review Finally, there are shown at the bottom of the display at indicators 521, patient information regarding the patient's white blood cell (WBC) count, body temperature, and microbiology, indicating the number of active microbiology reports available within the electronic health record of the patient—the specifics of the reports are accessed directly by clicking/touching this number and are displayed in a pop out window. Thus, in this manner, a caregiver can be provided with a master checklist that gathers various types of data about a patient and presents the information in a convenient manner, by which a caregiver may set the system for operating a ventilations system or monitoring such a system and automatically generate data for a reporting database.

FIGS. 8A and 8B are two portions of a table of example values for the patient monitoring interactive checklist of FIG. 7. Generally, each of the rows corresponds to one of the labels in FIG. 7. For each entry in the table, a description is given, along with a main rule and a secondary rule that may be triggered based on the patient's data. What is displayed for each factor is also shown here, as is the time range (time Rg)

FIG. 9 is a block diagram of a patient monitoring system. The system 900 may involve a number of networked computers and computer systems. The system 900 is shown for convenience here as being centered around a patient monitor system 908. The patient monitor system 908 extracts data from a number of data stores 902-904 and groups and formats the data for convenient display, such as in the manners discussed above. The data stores 902-904 may include, for example, data reflecting real time information about a patient (e.g., vital signs) as well as centrally stored electronic medical record information, among other things. Particular types of data are discussed with respect to FIG. 2 above.

A data extractor 910 may be programmed to identify and retrieve relevant data form the data stores 902-904. The extractor 910 may be programmed to implement heuristic rules that were determined by observing or surveying experienced caregivers with respect to the data points that they most often consult during particular phases of a patient's stay in a facility, such as in an ICU. A grouper 912 takes the particular data values retrieved by the extractor 910 and organizes the data into relevant groups, such as by organ type as discussed above. The extractor 910 or grouper 912 may also generate derivative data using one or more extracted data points.

A display formatter 916 provides for the generation of data for displaying patient information. The display formatter 916 may, for example, generate icons and arrange the icons and textual patient information provided by the extractor 910 and/or grouper 912 for display on a patient monitor 918. The particular display may vary, in certain implementations, based on the identity of the particular caregiver who is observing the monitor 918 or the class into which the caregiver falls (e.g., the caregivers particular job title, such as physician, nurse, attending physician, etc.).

The identity of the caregiver may be discerned by a caregiver identifier 914 that is in communication with a sensor 920. The sensor 920 may take a variety of forms such as an RFID sensor that obtains identifying information from an RFID chip in an identification badge worn by a caregiver when the caregiver is in proximity to the monitor 918 and thus in proximity to the sensor 920. The sensor 920 may also include a biometric sensor, such as a fingerprint reader. The caregiver may provide identifying information by other sensing mechanisms also, such as logging into a clinical system in various familiar manners. Each of these sensed objects may be considered to be a beacon that provides identifying information about the caregiver.

The identifying information may include an ID number such as form an RFID chip or bar code in or on an ID badge. The number may be returned by the sensor, and turned into a separate ID number by the caregiver identifier 914, such as the caregiver's employee number. The display formatter may then user the latter ID number to access a data store that stores formatting information for a display that is unique to the particular caregiver. The monitor 918 may thus, in this manner, provide for a display that is formatted in a manner that matches the job title of the caregiver (attending physicians may need information that is slightly different than that needed by nurses) or matches the actual caregiver (certain physicians may be more efficient if data is presented to them in a customized manner).

Figure 10:
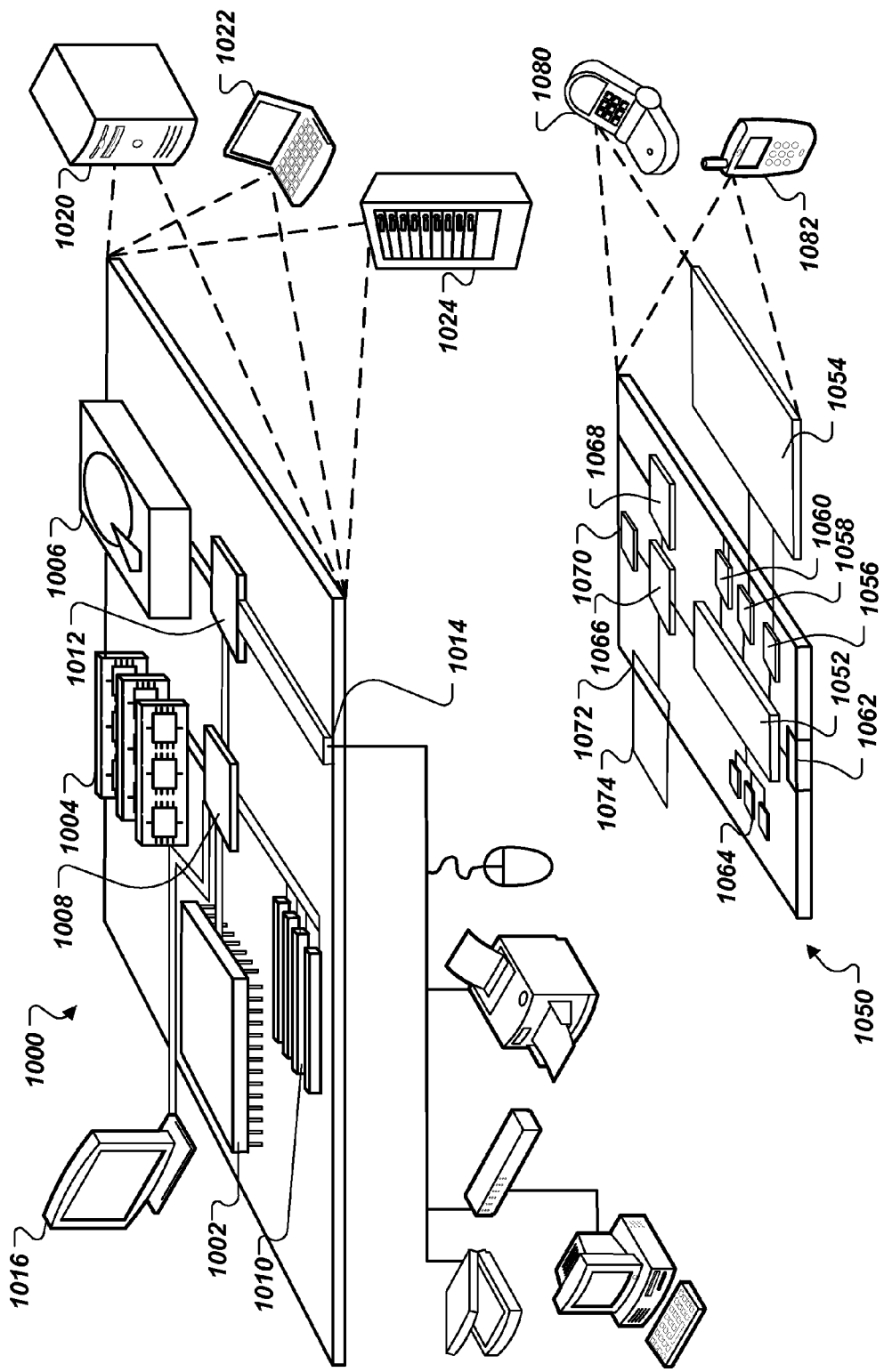
FIG. 10 is a schematic diagram of a computing device and a portable computing device that may be used to carry out the actions described in this document.

FIG. 10 shows an example of a generic computer device 1000 and a generic mobile computer device 1050, which may be used with the techniques described here. Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 1000 includes a processor 1002, memory 1004, a storage device 1006, a high-speed interface 1008 connecting to memory 1004 and high-speed expansion ports 1010, and a low speed interface 1012 connecting to low speed bus 1014 and storage device 1006. Each of the components 1002, 1004, 1006, 1008, 1010, and 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as display 1016 coupled to high speed interface 1008. In other implementations, multiple processors and/or multiple buses may be used, as appropriate, along with multiple memories and types of memory. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk.

The storage device 1006 is capable of providing mass storage for the computing device 1000. In one implementation, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1004, the storage device 1006, memory on processor 1002, or a propagated signal.

The high speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In the implementation, low-speed controller 1012 is coupled to storage device 1006 and low-speed expansion port 1014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. It may also be implemented as part of a rack server system 1024. In addition, it may be implemented in a personal computer such as a laptop computer 1022. Alternatively, components from computing device 1000 may be combined with other components in a mobile device (not shown), such as device 1050. Each of such devices may contain one or more of computing device 1000, 1050, and an entire system may be made up of multiple computing devices 1000, 1050 communicating with each other.

Computing device 1050 includes a processor 1052, memory 1064, an input/output device such as a display 1054, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the computing device 1050, including instructions stored in the memory 1064. The processor may be implemented as a chipset of chips that include separate and multiple analog and digital processors. The processor may provide, for example, for coordination of the other components of the device 1050, such as control of user interfaces, applications run by device 1050, and wireless communication by device 1050.

Processor 1052 may communicate with a user through control interface 1058 and display interface 1056 coupled to a display 1054. The display 1054 may be, for example, a TFT LCD (Thin-Film-Transistor Liquid Crystal Display) or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may be provide in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the computing device 1050. The memory 1064 can be implemented as one or more of a computer-readable medium or media, a volatile memory unit or units, or a non-volatile memory unit or units. Expansion memory 1074 may also be provided and connected to device 1050 through expansion interface 1072, which may include, for example, a SIMM (Single In Line Memory Module) card interface. Such expansion memory 1074 may provide extra storage space for device 1050, or may also store applications or other information for device 1050. Specifically, expansion memory 1074 may include instructions to carry out or supplement the processes described above, and may include secure information also. Thus, for example, expansion memory 1074 may be provide as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1064, expansion memory 1074, memory on processor 1052, or a propagated signal that may be received, for example, over transceiver 1068 or external interface 1062.

Device 1050 may communicate wirelessly through communication interface 1066, which may include digital signal processing circuitry where necessary. Communication interface 1066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, WiFi, or other such transceiver (not shown). In addition, GPS (Global Positioning System) receiver module 1070 may provide additional navigation- and location-related wireless data to device 1050, which may be used as appropriate by applications running on device 1050.

Device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, may include recorded sound (e.g., voice messages, music files, etc.) and may also include sound generated by applications operating on device 1050.

The computing device 1050 may be implemented in a number of different forms, as shown in the figure. For example, it may be implemented as a cellular telephone 1080. It may also be implemented as part of a smartphone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented patient information presentation method, comprising:
    identifying with a computer system, a plurality of groups of patient-related data that is a subset of possible groups of patient-related data that captures actual physical patient condition at the time of capture, to be displayed to a caregiver of a patient who is under care in a healthcare facility, the identifying based at least in part on a determined present physical condition of the patient, wherein the groups each represent multiple aspects about the patient;
    extracting, with a data extractor of the computer system programmed to identify relevant data for the patient, a subset of parameters that represent values for particular ones of the multiple aspects in each of the plurality of identified groups, so as to form a particular subset of data about physical patient condition from a first set of data;
    grouping, with the computer system, the subset of parameters into particular ones of the plurality of identified groups that each contain a plurality of parameters that represent physical patient condition, based on a determined relatedness among parameters in each of the plurality of groups, so as to form groups separate from a set of data from which the subset of parameters is extracted;
    providing, with a real-time patient-monitoring application executing on the computer system, data in a form for visual display to the caregiver that shows at least some of the subset of parameters arranged visually in the groups, with values for the plurality of parameters organized according to the groups to which each of the plurality of parameters corresponds, with individual ones of the groups that are displayed being selected based on the current physical condition of the patient, and the displayed groups being displayed in physical layout position relative to each other as a result of the identifying based on the determined present physical condition;
    receiving, in response to providing the data in the form for visual display in displayed groups input from a caregiver to order a procedure or change a therapy; and
    in response to receiving the input, ordering the procedure or change in therapy through an integrated computerized physician order entry system,
    wherein the extracting step selects parameters to be extracted based on a stored score that aggregates results from submitting to multiple caregivers questions regarding importance they placed on particular parameters in treating patients and receiving answers to the questions from the multiple caregivers.

2. The method of claim 1, further comprising identifying a plurality of subset groups of the parameters, where each of the plurality of subset groups is directed to a particular caregiver level that differs from others of the plurality of subset groups.

3. The method of claim 2, further comprising detecting the presence of an electronic caregiver beacon in proximity to a patient monitor, determining a caregiver level corresponding to a caregiver associated with the beacon, and displaying a subset of parameters directed to the determined caregiver level corresponding to the caregiver.

4. The method of claim 3, wherein the electronic caregiver beacon comprises an identification badge or biometric indicator.

5. The method of claim 1, wherein:
extracting the subset of parameters comprises extracting data from both a real time patient condition data store subsystem and an electronic medical record data store subsystem, and
providing data for visual display comprises showing areas that indicate (a) historical past data for the patient, (b) status of an investigation being undertaken for the patient, (c) current organ physiological status for an organ of the patient, and (d) healthcare provider actions taken for the patient.

6. The method of claim 1, further comprising detecting one or more indicia of organ failure for the patient and changing a display mode presented to the caregiver to provide information targeted to the organ failure, including a plurality of organ-related parameters previously identified as being useful to caregivers treating the organ failure, and to deprecate other information previously displayed on a display associated with the patient.

7. The method of claim 1, further comprising automatically determining an identity of a caregiver in proximity to a patient monitor and generating the display for presentation to the caregiver according to a custom layout for the identified caregiver.

8. A computing system, comprising:
a patient video monitor;
one or more processors;
memory; and
one or more programs, wherein the one or more programs are stored in the memory and configured to be executed by the one or more processors, the one or more programs including instructions, that when executed by a processor perform operations comprising:
identifying with a computer system, a plurality of groups of patient-related data that is a subset of possible groups of patient-related data that captures actual physical patient condition at the time of capture, to be displayed to a caregiver of a patient who is under care in a healthcare facility, the identifying based at least in part on a determined present condition of the patient, wherein the groups each represent multiple present conditions of the patient;
extracting, with a data extractor programmed to identify relevant data for the patient from a plurality of separate and independent data store subsystems, a subset of data points that represent values for particular ones of the multiple present conditions of the patient, and that are determined to represent parameters determined to have a higher relevance than other parameters considered by surveyed caregivers, as compared to other parameters that represent conditions of the patient that are not extracted, so as to form a particular subset of data about physical patient condition from a first set of data;
grouping the subset of data points into particular ones of the plurality of identified groups that each contain a plurality of parameters that represent physical patient condition, based on a determined relatedness among data points in each of the plurality of groups, so as to form groups separate from a set of data from which the subset of parameters is extracted; and
providing, with a real-time patient-monitoring application executing on the computer system, data in a form for presentation to a caregiver that shows visually at least some of the subset of data points arranged visually in the groups, with values for the plurality of parameters organized according to the groups to which each of the plurality of parameters corresponds, with individual ones of the groups that are visually displayed being selected based on the current physical condition of the patient, and the displayed groups being displayed in physical layout position relative to each other as a result of the identifying based on the determined present physical condition;
receiving, in response to providing the data in the form for visual display in displayed groups, input from a caregiver to order a procedure or change a therapy; and
in response to receiving the input, ordering the procedure or change in therapy through an integrated computerized physician order ent system,
wherein the extracting step selects parameters to be extracted based on a stored score that aggregates results from submitting to multiple caregivers questions regarding importance they placed on particular parameters in treating patients and receiving answers to the questions from the multiple caregivers.

9. The system of claim 8, wherein the operations further comprise identifying a plurality of subset groups of the data points, where each of the plurality of subset groups is directed to a particular caregiver level that differs from others of the plurality of subset groups.

10. The system of claim 9, wherein the subset groups are directed to different job titles of caregivers.

11. The system of claim 10, further comprising an electronic sensor arranged to detect the presence of a caregiver beacon in proximity to a patient monitor, wherein the operations further comprise determining a caregiver level corresponding to a caregiver associated with the beacon, and for displaying a subset of data points directed to the determined caregiver level corresponding to the caregiver.

12. The system of claim 11, wherein the caregiver beacon comprises an identification badge or biometric indicator.

13. The system of claim 8, further comprising a plurality of independent data stores storing the records, including a real time patient condition data store and an electronic medical record data store.

14. The system of claim 8, wherein the operations further comprise performing an identification of a caregiver in proximity to a patient monitor and generating the display for presentation to the caregiver according to a custom layout for the caregiver.

15. A computer-implemented patient information presentation system, comprising:
a data extractor operating on a computer processor system programmed to obtain a subset of data about a patient, including a physical condition of the patient at a time the data was captured, using heuristic rules directed to patient physical condition parameters determined to have a higher relevance than other parameters considered by caregivers and relating to present physical conditions of the patient, as compared to other parameters that represent physical conditions of the patient that are extractable but are not extracted, wherein the data extractor is programmed to operate in response to the computer processor system identifying a plurality of groups of patient-related data that includes actual physical condition data, the groups each representing multiple physical aspects about the patient, the subset being a group to be displayed to a caregiver of the patient and less than all groups that are displayable to caregivers, and the identifying based at least in part on a determined present physical condition of the patient;

a data grouper operating on the computer processor system, the data grouper programmed to identify particular parameters that correspond to particular ones of the plurality of groups and to select a subset of the identified parameters for display to a caregiver, so as to form groups separate from a set of data from which the subset of parameters is extracted based; and an electronic real-time patient monitor to (a) receive display data from the computer processor system, (b) display grouped patient physical information for at least some of the subset of data, with values for the plurality of parameters visually displayed and organized according to the groups to which each of the plurality of parameters corresponds, with individual ones of the groups that are displayed being selected to be displayed based on the current physical condition of the patient, and the displayed group being displayed in physical layout position relative to each other as a result of the identifying based on the determined present physical condition, (c) in response to the display of grouped patient physical information, receive input from a caregiver to order a procedure or change a therapy, and (d) in response to the received input, order the procedure or change in therapy through an integrated computerized physician order entry system, wherein the data extractor is programmed to select parameters to be extracted based on a stored score that aggregates results from submitting to multiple caregivers questions regarding importance they placed on particular parameters in treating patients, and receiving answers to the questions from the multiple caregivers.

16. The method of claim 1, wherein a first group of the groups presents data identifying a first body organ or organ group and showing multiple parameters about current functioning of the first body organ or organ group, each of the parameters displayed in the first group being selected and displayed based on determinations that the selected and displayed parameters are identified as being relied upon by multiple physicians, in contrast to other parameters relating to the first body organ or organ group that are not displayed, in identifying a condition of the first body organ or organ group, and a second group of the groups presents data identifying a second body organ or organ group and showing multiple parameters about current functioning of the second body organ or organ group.

17. The method of claim 1, further comprising screening the data points for data that indicates development of an organ failure of the patient, and automatically modifying the parameters of a particular group relating to the organ so that the modified parameters indicate presence of the organ failure.

18. The method of claim 1, further comprising weighting particular ones of the parameters in determining which parameters to provide for presentation in a group, the level of the weighting depending on a frequency with which the particular ones of the parameters have been used in medical decision making.

19. The method of claim 1, further comprising identifying a current patient medical status, and selecting which parameters to extract based on the identified current patient medical status.

20. The method of claim 1, further comprising periodically updating parameter values that are displayed in a first of the groups at a rate that differs for updating parameter values in a second of the groups.

21. The method of claim 1, further comprising detecting a particular physical medical syndrome to which the patient is being subjected, selecting parameters determined to be directed to the detected syndrome, and automatically displaying the parameters of the medical syndrome to the caregiver.

22. The method of claim 21, further comprising displaying a user-selectable object that, when selected by the caregiver, causes a determined treatment to be provided to the patient.

23. The method of claim 1, further comprising displaying to the caregiver the data on a mobile device of the caregiver that shows the groups of data in distinct different locations along with parameters for each of the groups of data.

24. The method of claim 1, wherein the displaying occurs in an organ status summary area of a visual display, and the method further comprises:

displaying a clinical information package in another area of the visual display that displays different parameter values for different organs or organ groups with a graphic identifying each particular organ or organ group, and a syndrome detection advisor in another area of the visual display that lists a plurality of medical syndromes for the patient and statuses of each of the plurality of medical syndromes.

* * * * *